United States Patent [19]

Gomberg et al.

[11] Patent Number: 4,918,315
[45] Date of Patent: Apr. 17, 1990

[54] NEUTRON SCATTER METHOD AND APPARATUS FOR THE NONINVASIVE INTERROGATION OF OBJECTS

[75] Inventors: Henry J. Gomberg, Ann Arbor, Mich.; Marcus McEllistrem, Lexington, Ky.

[73] Assignee: Penetron, Inc., Ann Arbor, Mich.

[21] Appl. No.: 200,133

[22] Filed: May 31, 1988

Related U.S. Application Data

[63] Continuation-in-part of Ser. No. 142,810, Jan. 11, 1988, Pat. No. 4,864,142.

[51] Int. Cl.$^4$ ............................................. G01N 23/204
[52] U.S. Cl. ........................ 250/390.04; 250/390.07; 250/390.08; 250/391
[58] Field of Search ..................... 250/390.04, 390.05, 250/390.07, 390.08, 390.12, 391, 392, 390.01; 378/57

[56] References Cited

U.S. PATENT DOCUMENTS

| | | | |
|---|---|---|---|
| 2,567,057 | 9/1951 | Crumrine | 250/390.04 |
| 3,146,349 | 8/1964 | Jordan | 250/390.04 |
| 3,832,545 | 8/1974 | Bartko | 250/390.04 |
| 3,997,787 | 12/1976 | Fearon et al. | 250/390.04 |
| 4,122,340 | 10/1978 | Smith, Jr. et al. | 250/264 |
| 4,251,726 | 2/1981 | Alvarez | 250/390.04 |

FOREIGN PATENT DOCUMENTS 2150737 7/1985 United Kingdom.
2151837 7/1985 United Kingdom.

OTHER PUBLICATIONS

Knoll, G. F., *Radiation Detection and Measurement*, published by John Wiley and Sons (New York), 1979, pp. 523-531.

Schrack et al., "Nuclear Fuel Assay Using Resonance Neutrons", *Dimension* (NBS), vol. 64, (No. 4), May, 1980, pp. 21-23.

*Primary Examiner*—Constantine Hannaher
*Attorney, Agent, or Firm*—Krass and Young

[57] ABSTRACT

A system and method for the inspection and/or search for concealed objects impinges a monoenergetic neutron beam upon an object, notes the energy distribution of the neutrons scattered from the object and correlates the energy/intensity distribution of the scattered neutrons with the presence or absence of particular elements. The invention may be utilized to obtain qualitative or quantitative data regarding the composition of the object under interrogation.

26 Claims, 9 Drawing Sheets

NEUTRON SCATTER METHOD AND APPARATUS FOR THE NONINVASIVE INTERROGATION OF OBJECTS

RELATED APPLICATION

This application is a continuation-in-part of U.S. patent application Ser. No. 142,810, filed Jan. 11, 1988, now U.S. Pat. No. 4,864,142.

FIELD OF THE INVENTION

This invention relates to methods and apparatus for noninvasively assessing the composition or contents of objects such as closed or otherwise inaccessible containers. In particular, the present invention relates to a method and apparatus for detecting materials such as hazardous substances or other contraband by employing scattered neutrons to effect such inspection.

BACKGROUND OF THE INVENTION

The need for rapid, safe and non-intrusive inspection systems has been increasing greatly. Typical of this need is the necessity of inspecting parcels and packages at transport terminals, post offices and freight depots.

The cost of international travel has decreased significantly recent years and with this decrease there has been a dramatic increase in the volume of international passengers. Concomitant with this increase in the number of travelers has been an increase in the smuggling of contraband via commercial carriers. By contraband it is meant any substance whose trade or transport is restricted by law. As used specifically herein contraband shall refer primarily to hazardous materials such as explosives and narcotics, and shall include military explosives such as mines and ammunition disposed in vehicles, buildings, packages or atop or beneath the surface of the earth.

Because of an increasing demand for narcotics and because of increasing world tension there has been a significant escalation in the transport of such contraband across international borders. It is desirable to interdict such commerce, but because of the greatly increased volume of international traffic, such interdiction becomes very difficult.

While it is theoretically possible to inspect every parcel or item of baggage passing across a border, through an air, rail or sea terminal or through a post office, such inspection would be very costly in terms of wasted time and impeded commerce; furthermore, smugglers frequently resort to the use of packages having hidden compartments, false bottoms and the like which may be overlooked in all but the most scrupulous inspection.

Also, there is a need for explosive detection techniques which may be adapted to quickly scan the surface or subsurface of the earth for mines or other buried explosives. It is preferred that such techniques be reliable, rapid and capable of conducting such inspection from a distance, as for example in a fly-over inspection.

Accordingly, there is a need for a rapid method for detecting the presence of contraband and it is preferred that the technique be noninvasive or nonvisual, that is to say be capable of inspecting the contents of a closed container, without necessitating opening of the container. In many instances a container will not be "closed" in the sense of being sealed, but may be partially opened, porous or permeable; however, as used herein a closed container shall include all such containers not readily subject to visual inspection and shall include parcels, packages, and envelopes as well as structural components of buildings and vehicles. In some instances mines or other military explosives are disposed beneath the soil or waters of the earth's surface, whereas in other instances such devices are "laid" upon the surface of the earth and rely upon camouflage or natural cover to hide them. Therefore, for purposes of this disclosure such devices shall also be deemed to be enclosed.

Such a noninvasive method would save time as well as be highly accurate insofar as false bottoms and the like would not present a source of confusion. It is required that any such inspection technique not harm the articles being inspected or present any lingering physical hazards to the owners of the articles.

Magnetic techniques are employed for the detection of metallic articles such as weapons however, nonmetallic items such as explosives or narcotics are not detected by such techniques. X-ray inspection is frequently employed to view the contents of closed packages, but cannot identify the composition of the observed materials. Many explosives and narcotics have unremarkable X-ray absorption characteristics and hence are indistinguishable from more normal items of commerce. Therefore it may be seen that heretofore employed magnetic or X-ray techniques cannot detect many items of contraband.

The use of neutrons for analysis of the contents of closed packages has previously been investigated. Thermal neutron activation analysis (TNAA) is an analytical technique which has been known and utilized for some time to perform quantitative and qualitative analyses. In this technique relatively low energy neutrons are employed to bombard a sample under investigation. The nuclei of component atoms thereof capture these neutrons and become radioactive. These newly formed radioactive isotopes then undergo atomic decay and emit energetic particles and/or photons in the process. By identifying the emitted radiation, the composition of the sample may be determined. While TNAA techniques are capable of identifying various chemical elements they are not well suited for the high volume inspection of closed containers, as for example at airport terminals, border stations, post offices and the like. TNAA of necessity renders a sample being inspected radioactive and this radioactivity may persist for a significant period of time after completion of analysis thereby presenting a potential health hazard. In many instances, the exact composition of the sample under investigation is not known and consequently the duration of the induced radiation cannot be told beforehand. Thus many inspected items will have the potential of remaining radioactive for fairly long periods of time. Furthermore, TNAA techniques are not particularly efficient for detecting nitrogen or carbon, major components of narcotics and explosives, because the capture cross section for these elements is quite small as compared to that of metals and other heavy elements. Consequently if a usable signal is to be produced, a relatively high neutron flux must be employed, and this high flux can induce significant residual radioactivity in objects being inspected. Additionally, TNAA is very insensitive to oxygen, another element of interest in narcotics and explosives.

Neutron absorption analysis is another technique proposed for the noninvasive inspection of closed containers. In such a process, the absorption of high energy neutrons as they pass through an object is measured. Certain elements are very strongly absorbing of neutrons whereas others are not and this absorption may be utilized to characterize a sample. For example, neutron absorption techniques may be utilized to look for nitrogen or other elements typically associated with narcotics or explosives. The main problem with neutron absorption analysis is that there are a number of elements having very strong absorption signatures which interfere with the detection of the element of interest. For example, boron, as Well as Various rare earth elements have significant neutron absorptions which can mask or otherwise interfere with the absorption of neutrons by nitrogen. Additionally, the absorption of neutrons can create the aforementioned problems of lingering radioactivity.

U.S. Pat. No. 3,997,787 discloses a dual stage analysis system for the detection of explosives in closed packages. The system relies upon the use of thermal neutron activation to detect the presence of oxygen in the contents of the container and neutron absorption to detect the presence of nitrogen therein. The presence of significant quantities of both elements is taken as an indication that explosives may be present in the container. The method of U.S. Pat. No. 3,997,787 suffers from the aforementioned shortcomings of both neutron absorption and neutron activation techniques.

It has now been found that neutron scatter techniques may be adapted for the qualitative and quantitative analysis of the contents of closed packages. Such techniques employ elastically scattered neutrons and as will be explained in greater detail, do not induce significant residual radiation in items and provide for rapid and accurate analysis while minimizing interference from other elements which may be present.

In accord with one embodiment of the present invention it has been found that the resonant elastic scattering of neutrons may be employed with advantage in the detection of contraband in closed containers. Resonant elastic scattering "NRES" is a process whereby neutrons impinge upon and are scattered with minimum energy loss from the nuclei of target atoms. The scattering is typically isotropic insofar as the neutrons are uniformly scattered in all directions from the target nucleus. In those instances where resonant scattering of neutrons is backwards in the general direction of the source, the technique is referred to as back scattering. Since the scattering is elastic no residual radioactivity is created in the target atom. Neutron resonant elastic scattering also has a further advantage in relation to neutron absorption or activation techniques and that is due to the fact that the elastic scattering cross section for neutrons is much larger than the absorption cross section and this difference is greatest for the light elements where scattering cross sections are typically 100 to 1000 times greater than absorption cross sections. Such large cross sections make possible the use of relatively low fluxes of neutrons for resonant elastic scattering analyses.

Neutron resonant elastic scattering techniques are also highly specific for particular elements. That is to say each element has a unique elastic scattering spectrum characterized by the presence of resonance peaks therein, said peaks representing particular neutron energies at which the elastic scattering cross section of a given element is large. Resonance spectra may be readily measured by varying the energy of a monochromatic neutron beam and measuring the intensity of elastically scattered neutrons as a function of beam energy. It should be noted that by the term "monochromatic" is meant a beam having a relatively narrow distribution of energies, analogous to a beam of light of a single wavelength; such a beam may also be referred to as "monoenergetic." As will be explained in greater detail hereinbelow, resonant elastic scattering techniques form the basis for a highly specific and accurate analytical system adapted for the non-invasive interrogation of objects, such as objects which are buried or in closed containers.

Each element has a particular neutron elastic scatter spectrum characterized by a number of particular resonance peaks which can be used to establish the presence of and/or quantify the amount of that particular element present. Likewise, a particular chemical compound will have a unique neutron scatter spectrum reflecting the relative percent of the various component atoms thereof. Contraband items it will thus be appreciated will each present a unique neutron resonant elastic scatter spectrum.

Even more significantly various classes of contraband or other hazardous items will be characterized by certain common features in their resonant scatter spectra, reflecting certain ranges or proportions of various component atoms. For example, explosives broadly fall into two common classes. The first class is referred to as "oxidizing explosives" and its members derive their power from the very rapid oxidation of carbon and hydrogen. Nitrates are the most effective fast acting sources of oxygen for such reactions. Oxidizing explosives are characterized by an oxygen-nitrogen ratio which may range from 1 to 4. Some oxidizing explosives are listed in Table 1 below.

TABLE 1

|  | Atomic Ratios | | |
| --- | --- | --- | --- |
|  | H:N | O:N | C:N |
| Ammonium Nitrate $NH_4NO_3$ | 2.0 | 1.5 | 0 |
| Nitroglycerin $C_3H_5N_3O_9$ | 1.67 | 3 | 1 |
| Nitromethane $CH_3NO_2$ | 3 | 2 | 1 |
| Tetranitromethane $C(NO_2)_4$ | 0 | 2 | 0.25 |
| RDX $C_3H_6N_6O_6$ | 1 | 1 | 0.5 |
| Tetryl $C_6H_5N_5O_8$ | 1 | 1.6 | 1.2 |

A second class of commonly employed explosives derives its power from the high energy disassociation of metastable, oxygen-free nitrogen compounds such as azides. In such explosives, the oxygen-nitrogen ratio is generally 0, the hydrogen-nitrogen ratio is 1 or less and the carbon-nitrogen ratio is lower. Some such explosives are listed in Table 2.

TABLE 2

|  | Atomic Ratios | |
| --- | --- | --- |
| Dissociating Explosives | H:N | C:N |
| Hydrazine Azide $N_2H_4HN_3$ | 1 | 0 |
| Guanyl Azide $CH_6N_4$ | 1.5 | 0.25 |
| Tetrazene $CH_7N_9O$ | 0.78 | .11 |

Reference to the ratios listed in the tables above indicates that specific compositional ranges may be associated with specific types of contraband explosives. By reference to a plurality of such compositional ranges false readings which could stem from looking at the ratio of a single pair of elements would be eliminated. For example, acrylonitrile, the basic component of commercial plastics such as Orlon has a carbon-nitrogen of three and hydrogen-nitrogen ratio of three.

Based upon a simple analysis for the presence of nitrogen Orlon might be mistaken for an explosive compound. However, the oxygen-nitrogen ratio of acrylonitrile is 0 therefore it can be eliminated as being an oxidizing type explosive. Furthermore, the hydrogen-nitrogen ratio is three, whereas typical disassociating type explosives have a lower hydrogen-nitrogen ratio therefore acrylonitrile can be disqualified as being a dissociating type explosive. Melamine, another common plastic has an empirical formula of $C_3H_6N_6$. Consequently, H:N ratio is 1 and its C:N ratio is 0.5. This might allow it to be confused with RDX; however, the O:N ratio is 0, therefore melamine can be readily distinguished from such explosives.

Neutron resonant scatter analysis enables one to rapidly and reliably obtain a plurality of ratios of elements in a sample and, since what is being measured are ratios and not absolute quantities, the process is effectively "self-standardizing."

Similar ratios may be established for narcotic contraband. Referring now to Table 3, there are shown elemental ratios for particular narcotics.

TABLE 3

| Narcotics | Atomic Ratios | | |
|---|---|---|---|
| | H:N | C:N | O:N |
| Morphine | 19 | 17 | 3 |
| Cocaine | 21 | 17 | 4 |
| Heroin | 23 | 21 | 5 |
| Methadone | 27 | 21 | 1 |
| Codeine | 23 | 18 | 3 |

It will be seen that there are particular atomic ratios associated with narcotic materials. Referring now to Table 4, there are shown atomic ratios for various articles of commerce which may be expected to be found in luggage, parcels or the like.

TABLE 4

| Articles of Commerce | Atomic Ratios | | |
|---|---|---|---|
| | H:N | C:N | O:N |
| Wool | 4.8 | 3.3 | 1.1 |
| Silk | 4.5 | 3.0 | 1.2 |
| Leather | 4.8 | 3.1 | 1.3 |
| Acrylonitrile | 3+ | 3+ | 0 |

It is apparent then that there are distinct groups of atomic ratios associated with explosives, narcotics and innocuous materials and these ratios may be utilized as a basis for the determination of the presence of contraband in a container without the need for the visual inspection thereof.

In addition to the use of a ratio-type analysis, neutron resonant scatter analysis may also be employed to simply determine the presence or absence of particular elements which may be expected to occur in contraband materials. For example, nitrogen is present in virtually all explosives, while mercury, lead or other heavy metals are frequently found in explosive primers. Similarly, sulfur, phosphorous and potassium are frequently found in black powder explosives and elements such as boron and beryllium are present in nuclear devices; thus the presence of such atomic species may be indicative of the presence of explosive contraband.

In an embodiment of this type, a single resonance peak or group of peaks characteristic of a given element is scanned for. Magnitude of the peak will give some information regarding quantities of the species of interest. This single element embodiment is well suited for simple, rapid scanning, and may be used to "pre-screen" items prior to implementing a full ratio type scan.

In accord with another embodiment of the present invention, it has been found that neutron elastic backscatter techniques, "NEBS" which do not necessarily rely upon the use of resonant scattering may also be employed with significant advantage in the inspection of items within closed packages. Neutron elastic backscatter techniques referred to herein as "NEBS" techniques involve the impingement of a monoenergetic beam of neutrons upon an object. The various atoms within the object will scatter the beam, generally in all directions. The scattered neutrons undergo a change in energy and this change will be dependent upon the energy of the incident neutrons, the scatter angle, as well as the atomic mass of the target atoms. It has been found that significant advantage may be enjoyed by analysis of the neutrons which are scattered primarily in the direction from whence they came, such neutrons being referred to as backscattered. The energy of backscattered neutrons is generally given by the formula:

$$E_{back} = E_{in}\left(\frac{A-1}{A+1}\right)^2$$

wherein $E_{Back}$ refers to the energy of the backscattered neutrons, $E_{In}$ refers to the energy of the incident neutrons and A is the atomic mass of the scattering atom. It will thus be appreciated that for a neutron beam of a given energy there will be a particular energy of backscattered neutron corresponding to the atomic mass of the scattering atom.

Problems have sometimes been encountered in the use of the resonant neutron scatter techniques previously described insofar as resonance peaks of atoms of interest frequently overlap making measurement difficult or impossible. NEBS techniques need not rely upon the measurement of resonance energies; but rather, such techniques analyze the energy/intensity spectrum of neutrons backscattered from an object to determine its composition.

If the energy of the incident beam in a NEBS analysis is varied it will be appreciated that the energy/intensity spectrum of the backscattered neutrons will change. By comparing two spectra made at different energies, both absolute amounts and ratios of particular elements may be determined with minimal interference from overlapping peaks, as will be explained in greater detail hereinbelow.

While the NEBS technique of the present invention need not rely upon resonance measurements it may obviously make use of incident neutron beams having an energy selected to create a resonant backscatter condition for a particular element of interest. The technique may be employed in conjunction with two incident beam-energies, one being of a resonance producing energy and the other being off resonance. Comparison of the backscatter spectra for the two beams will show significant change in the intensity of backscatter neutrons attributable to the element having the resonance energy and by comparison of such spectra, contribution from the resonance producing element may be quantified.

It has been found that scattered neutrons frequently have a significant anisotropic component to their distribution and it has further been found that this component is often at least partially directed, in the backscatter direction. In such instances, the use of backscatter techniques confers additional advantage of enhanced signal intensity. The NEBS technique has also been found advantageous for detecting materials of medium molecular weight such as silicon, sodium, iron, calcium, chromium and nickel.

NEBS techniques may be employed both to determine the ratios of various atomic species in an object or to determine the presence of a single element and in this respect may be employed in a manner quite analogous to, and utilizing the ratios established for, the previously described resonant scattering techniques.

The neutron scatter analysis techniques of the present invention confer significant advantage in the detection of contraband material insofar as such materials may be reliably detected in the presence of relatively large amounts of innocuous substances. Furthermore, the detection can be done without need for opening containers or otherwise unduly delaying commerce. The processes may be readily adapted for scanning structural components of buildings and vehicles as well as for scanning the earth at or just below the surface for buried or submerged objects of interest. In contrast to thermal neutron activation analysis techniques, the techniques of the instant invention do not induce high levels of radioactivity in articles being inspected, and accordingly delay time for "cool down" and hazards to personnel are eliminated. Techniques of the present invention are readily adaptable to full automation and computer control and accordingly can provide for high volume/low cost nonvisual identification of the composition of a variety of items. These and other advantages of the instant invention will be apparent from the drawings, description and claims which follow.

BRIEF DESCRIPTION OF THE INVENTION

There is disclosed herein apparatus for the non-invasive inspection of an object to determine the presence of at least one preselected element therein. The apparatus comprises a neutron beam source for generating a monoenergetic beam of neutrons and impinging that beam upon an object. The object scatters the beam so as to provide a group of multienergetic scattered neutrons having an energy distribution which is characteristic of the scattering atom and the apparatus further includes a detector disposed to receive at least a portion of the group of scattered neutrons and to provide a signal corresponding thereto. The apparatus also includes an analyzer in operative communication with the detector and operative to (1) receive the detector output signal (2) analyze the signal to determine the intensity of the scattered neutrons as a function of their respective energies and (3) measure the intensity of scattered neutrons at a preselected energy which is indicative of the scattering of the monoenergetic beam by one of at least said one preselected element.

In other embodiments, the apparatus further includes a neutron beam controller operative in combination with the neutron beam source to sequentially provide at least two monoenergetic neutron beams having different energies and to sequentially impinge those beams upon the object so as to provide at least two groups of multienergetic scattered neutrons. In this embodiment the analyzer is further operative to determine the intensity of scattered neutrons as a function of energy for each of the two groups of scattered neutrons and to further determine the difference between the intensity of scattered neutrons for the first group at a first preselected energy which is indicative of the scattering of that beam by a particular preselected element and the intensity of scattered neutrons from the second group at a second preselected energy which is indicative of scattering of a second monoenergetic beam by the same preselected element. The controller is further operative to correlate the difference between the two intensities with the scattering contribution of the preselected element.

In another embodiment, the object being analyzed includes at least two preselected elements and the neutron beam source is adapted to provide a single monoenergetic beam of neutrons. In this embodiment the analyzer is further operative to measure intensity of scattered neutrons at two preselected energies, a first indicative of scattering of the monoenergetic beam by a first preselected element and the second indicative of the scattering of that same beam by a second preselected element. The analyzer is further operative to correlate the intensity of the first and second preselected energies with the relative amounts of the first and second element present. This particular embodiment may be further modified to provide two monoenergetic beams of different energy and to analyze two separate sets of scatter data to determine either relative or absolute amounts of the preselected elements.

In particular modes, the neutron beam source is operative to generate a monoenergetic pulse of neutrons and the analyzer is operative to measure the time of flight in which the scattered neutrons travel from the object to the detector. The time of flight is inversely proportional to the velocity of the neutrons and the analyzer correlates the time of flight with the energy of the scattered neutrons. In particular embodiments, the apparatus is configured for the measurement of the energy of the backscattered neutrons. The invention further includes a method employing the aforementioned apparatus.

DETAILED DESCRIPTION OF THE INVENTION

I. Resonant Scatter Techniques

Figure 1:
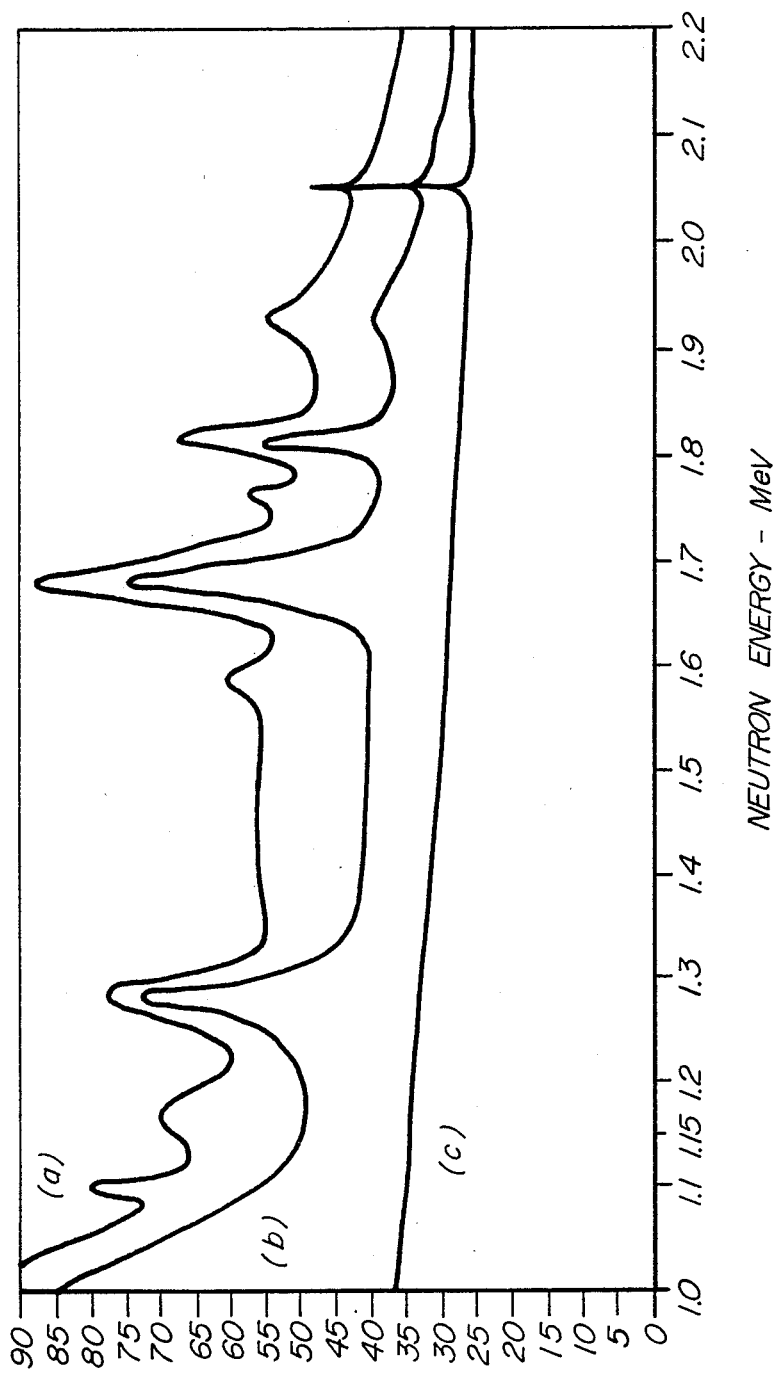
FIG. 1 is a depiction of neutron resonant elastic scatter spectra for (a) an explosive (b) a non-explosive polymer, and (c) a hydrocarbon.

Although briefly discussed previously, the principles of the resonant scatter techniques of the present invention will be recapitulated. Each element, and in fact each isotope has a unique neutron resonant scattering spectrum and this spectrum can be utilized to determine the composition of materials in closed containers. The technique is basically a spectroscopic analysis and the spectra are obtained by directing a beam of monoenergetic neutrons at an object, and detecting the scattered neutrons. As the energy of the incident neutrons is varied the intensity of the scattered neutrons will change. There are resonance peaks in the scatter spectrum, that is to say neutrons having certain energies are scattered more efficiently from particular atomic species than are neutrons with different energies. The scatter spectrum will thus include one or more maxima corresponding to those points where resonant scattering occurs. For example, oxygen has resonance peaks at approximately 0.434 Mev, 1.312 Mev, 1.907 Mev, 2.888 Mev and 3.442 Mev; nitrogen has resonance peaks at 0.432 Mev 0.997, 1.116 Mev; 2.230 MeV, 2.749 MeV, and 3.510 MeV while carbon exhibits resonances at approximately 2.077 Mev and 2.818 Mev. Additionally, sulfur has a resonance at 0.103 MeV, boron at 0.430 MeV, beryllium at 0.029 and 0.390 MeV, phosphorous at 0.157 MeV, potassium at 0.058 and 0.068 MeV and fluorine at 0.049 MeV. (All of the foregoing data are from Brookhaven National Laboratory Report #325, third edition, and are believed to be accurate. Should the values later be determined to differ, the principles and relationships disclosed herein are still valid.) In addition to these peaks, the resonant scatter spectra of these elements also exhibit many other peaks at different energy levels.

The location of the peaks in the spectrum may be correlated with the atomic species from which scattering is occurring and the absolute magnitude of those peaks may be correlated with the number of scattering nuclei present. By looking for a "signature" spectrum, that is to say a particular peak or group of peaks associated with a given element, the presence as well as the relative quantity of that element can be assessed. By measuring peaks corresponding to different elements, the ratios of particular atoms present in a sample under investigation may be determined. It has been found that items of contraband such as narcotics or explosives have particular ranges of ratios for elements such as carbon, oxygen and nitrogen, which ranges may be utilized as signatures for such materials. For example, it has been found that most explosives have an oxygen to nitrogen ratio within the range of 1.0 to 4.0 and a carbon to nitrogen ratio which is in the range of 0 to 2.5. Disassociating type explosives have a carbon to nitrogen ratio which is between 0 and 0.5 and a hydrogen-nitrogen ratio which is between 0.5 and 2.0. Narcotics in contrast, have an oxygen-nitrogen ratio which is typically in the range of 1 to 5 and a carbon-nitrogen ratio which is 16 or greater.

Problems can occur because certain resonance peaks of particular atoms will overlap and interfere with measurement of other atoms of interest; for example, the 0.432 MeV resonance of nitrogen interferes with the measurement of the 0.434 MeV resonance for oxygen. There are however, many distinctive resonances for each particular nucleus which are free from significant interference particularly if adequate monochromaticity of the neutron source is maintained.

Effective detection of the neutrons will depend upon the monochromaticity, energy range and intensity of the neutron source as well as the sensitivity of the detectors for scattered neutrons. Accordingly, collimation and shielding will be needed at the source and the detectors to attenuate background signals arising from spurious neutrons not scattered by the sample.

There are in addition, pulse height, pulse shape and pulse matching techniques which help select desired signals from total input. For example, the height of the detected pulse, at a given scattered neutron energy may be correlated with the atom responsible for that scattering. In theory, techniques of this type are more precise than time of flight techniques because the energy distribution of neutrons scattered from a group of differing atoms is much larger than the temporal distribution of those neutrons. In general though, it is easier to obtain a relatively intense, temporally resolved signal, therefore time of flight techniques are usually employed. Pulse height techniques may be combined with time of flight resolution to obtain three dimensional information about the composition of the scattering object. Pulse height may be employed to determine composition, while time of flight may be employed to select a stratum in the object for correlation with the various energies of scattered neutrons, so as to spatially resolve the composition of the target object.

Referring now to FIG. 1, there is shown a set of neutron resonant scatter spectra for some particular materials of interest. Curve C is representative of an unsaturated hydrocarbon, namely propylene and as indicated includes only one resonance peak at approximately 2.08 MeV. Curve B is the resonance scatter spectrum of a similar, nitrogen-free chemical compound which further includes oxygen therein. It will be noted that the spectrum becomes much more complex owing to scattering from oxygen atoms. Curve A is a spectrum for RDX, a common plastic-type explosive. It will be noted that while the compositions of the three materials depicted are relatively similar, the spectrum of the RDX includes particular resonance peaks not found in those of the other compounds. These peaks are correlatable with nitrogen content and may be utilized to establish oxygen-nitrogen ratios and carbon-nitrogen ratios as previously mentioned. From the spectra of FIG. 1 it should be apparent, the manner in which the method in the apparatus of the present invention may be employed to detect contraband substances.

In addition to the use of ratios for analysis, contraband may be more simply detected by analysis of scattered neutrons to determine the presence or absence of particular elements of interest. Since each element has a characteristic scatter spectrum, such spectra may be employed as a fingerprint to detect the presence of elements of interest such as nitrogen.

Figure 2:
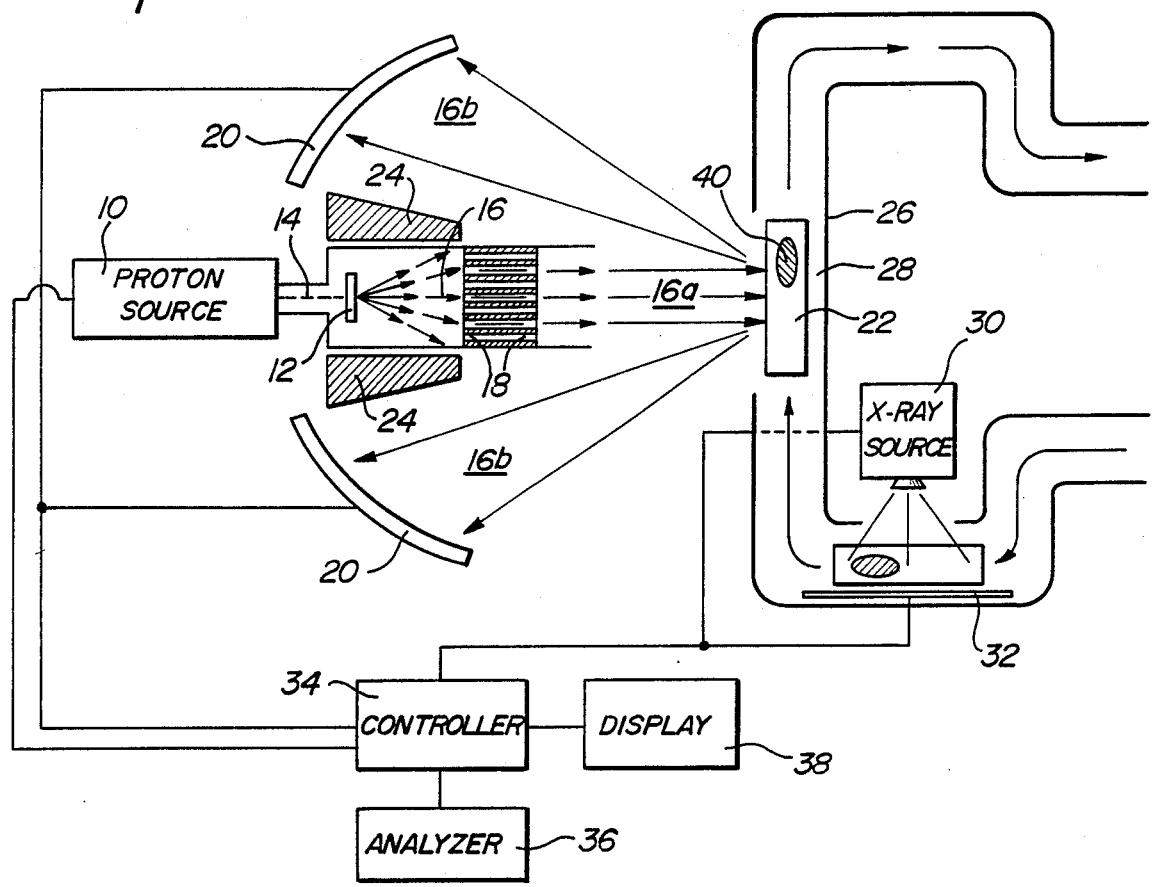
FIG. 2 is a schematic depiction of one particular apparatus structured in accord with the principles of the present invention as disposed to interrogate closed containers to detect the presence of contraband.

Referring now to FIG. 2, there is shown a schematic depiction of one particular contraband detection system structured in accord with the principles of the instant invention. The system of FIG. 2, is adapted to project a beam of neutrons onto an object, such as a closed container, collect neutrons backscattered therefrom and analyze them to determine the likelihood of contraband being within the closed container.

The system of FIG. 2 includes a neutron source capable of providing neutrons with a varying range of energies. There are many different types of neutron sources available to those with skill in the art. One particularly easy to control source is depicted in FIG. 2 and is comprised of a proton source 10 adapted to bombard a target 12 with a beam of energetic protons 14. The target 12 is fabricated from a material which generates neutrons when struck by protons. Lithium is one such preferred material, although other material such as carbon, oxygen, deuterium, tritium, and helium may be employed as target materials either in the form of pure materials or as compounds thereof, as is known to those of skill in the art.

When bombarded by a proton beam, a lithium atom absorbs a proton and emits a neutron, being converted to beryllium in the process. The energy of the emitted neutron will be a function of the energy of the incident proton and accordingly, neutron beam energy may be controlled by controlling the proton source 10. While the instant invention may be practiced with neutrons having a wide range of energies, it has been determined that for most contraband, the range of approximately 0.1-2.2 MeV will be sufficient, however this range may be readily extended to 4.0 MeV and beyond, particularly when high penetration is required, as for example when the object being interrogated is large or dense. Likewise, for detection of particular elements a lower energy range may be appropriate, particularly since the elastic scatter cross section is larger at lower energies.

It is estimated that if neutron resonant scatter peaks are to be determined with precision, the energy spread (i.e. monochromaticity) of the neutron beam should be kept to several, (i.e., twenty KeV); that is to say, the bandwidth of neutron energy should be approximately 20 KeV at the half maximum for each nominal energy level. Since a one KeV energy spread can be readily maintained with presently available sources, the system of the present invention is operating well within the state of the art.

The neutrons 16 emitted by bombardment of the target 12 are generated in a random direction and accordingly the apparatus must include a collimator 18 to define a parallel neutron beam. As depicted, the collimator is a relatively thick body of neutron absorbing material such as polyethylene loaded with boron and including a plurality of elongated channels therethrough. The channels function to permit only those neutrons traveling in approximately parallel paths to pass. Neutron collimators are known to those with skill in the art and there are many designs and materials which may be incorporated herein. For example, instead of the aforementioned polyethylene, the collimator may be a water filled body having channels extending therethrough.

The apparatus of FIG. 2 further includes one or more neutron detectors 20 disposed so as to receive neutrons backscattered from the object 22 being interrogated. These detectors may for example be scintillation-type detectors as are well known to those of skill in the art. While the embodiment of FIG. 2 utilizes detectors disposed to sense backscattered neutrons, the scattering process is quite isotropic. Therefore, the detectors may be placed in numerous other positions. It is essential, however, that care be taken in the placement of the detectors 20 so as to avoid generation of spurious signals from neutrons other than those scattered from the object 22 under investigation. Accordingly, the apparatus will include appropriately placed and shaped neutron shields 24 disposed so as to absorb significant numbers of stray neutrons.

Rejection of spurious signals and an increase in selectivity may be achieved by use of a time of flight detection technique wherein the neutron source is operated in a pulsed mode so as to emit short preferably nanosecond bursts of neutrons and the detector 20 is energized in synchrony so as to detect only those neutrons in a particular burst and having a transit time equal to the interval required to travel from the source to the object 22 being interrogated and back to the detector. In this manner neutrons scattered by atmospheric oxygen or nitrogen or by other objects not under interrogation will be rejected.

The inspection system further includes a conveyer 26 for moving objects into position for interrogation. As depicted, the conveyer system 26 is fabricated from a material relatively impervious to neutrons so as to function as a shielding member. The conveyer system includes an interrogation station 28 having an opening through which the neutron beam may pass. The conveyer system 26 is configured to define a tortuous path so as to baffle the flow of neutrons therethrough. In this manner, the insertion and removal of objects into the system is facilitated while eliminating the need for shielding at the exit and entrance regions thereof. In the depicted embodiment, the system further includes means for X-ray scanning of objects along with with neutron interrogation thereof. Toward this end the apparatus includes an X-ray source 30 and an X-ray detector 32 disposed so as to generate an X-ray image of an object concomitant with neutron interrogation.

As depicted, the apparatus is controlled by a controller 34 which, as will be elaborated upon in greater detail herein below, may be a computer or microprocessor. The controller 34 receives inputs from the neutron detectors 20, the proton source 10, the X-ray source 30, the X-ray detector 32 and controls those items in response to such inputs. Also associated with the controller 34 is an analyzer 36, adapted to analyze the signal from the neutron detectors so as to determine the presence of a preselected element and/or the ratios of particular atomic species as indicated by the scatter signal. The controller also has a display device 38, such as a cathode ray tube or the like associated therewith for displaying the results of the inspection. Display may be in the form of alpha-numeric printout indicating the likelihood of contraband being in the container, or the display may comprise a visual display of the contents of the container indicating by color, or alpha-numeric code, regions of suspect content. The controller 34 may be utilized to merge an X-ray image with a neutron generated image in a composite fashion so as to better indicate the content of a package.

In operation of the device of FIG. 2, a beam of protons 14 is generated by the proton source 10 and directed to impinge upon the lithium target 12 so as to generate a beam of neutrons 16. The controller 34 varies the energy of the proton beam 14 in accord with a predetermined program so as to vary the energy of the resultant neutron beam 16. This variation may be in a continuous manner, or may be step-wise over the range of interest. In those instances where the beam energy is varied in a step-wise manner, it will be desired that the steps correspond to at least one particular resonance energy of interest.

Upon bombardment by the proton flux 14, the target 12 emits neutrons 16 which are collimated by the collimator 18. The collimated beam 16a is directed toward the object 22 being interrogated in the interrogation region 28 and that beam 16a impinges upon the object 22 penetrating thereinto and scattering from objects inside. As indicated, the container 22 under interrogation includes therein an item 40 of contraband. Neutrons backscattered from the container 22 rebound and are collected by the detectors 20. It will be appreciated that the scattered beam 16b is generally spherical in shape and accordingly it may be desirable to configure the detectors 20 as a hemispherical or parabolic array.

The detectors 20 produce a signal corresponding to the intensity of neutrons received thereby and this signal is communicated to the controller 34 for analysis by the analyzer 36.

In the analyzer 36 the intensity of the neutron signal is correlated with the energy of the incident neutron beam 16a and this signal utilized to determine the resonant scatter spectrum. This information may be further processed to identify either a single element or to determine relative ratios of elements. Once these ratios are determined, they are compared with ratios for known contraband. If a match is obtained the controller 34, signals the display 38 so as to give an alarm indication.

Obviously, many refinements of the foregoing technique will be apparent to one of skill in the art. For example, sensitivity of the system may be increased by operation in a pulsed or time of flight mode as previously discussed whereby neutron energy is directed onto the container 22 in short bursts. The operation of the detectors 20 is synchronized with these bursts so that the detectors 20 only sense neutrons produced by the bursts and scattered from the container. In this manner, spurious signals from residual radiation, neutrons scattered by the atmosphere and the like do not interfere with operation of the system thereby increasing selectivity. In other variations, the transport system 26 may include additional stations for visual or magnetic scanning of parcels and may also include "cool down" sections to allow for decay of any residual radiation induced by the neutron beam, although in a system of this type employing elastic scattering rather than absorption of neutrons, such residual radiation will be minimal.

Relatively small objects may be interrogated in their entirety by a single beam of neutron energy however, in the instance of larger objects it may be desirable to obtain a spatial resolution of the contents so as to determine the exact location of the suspect contraband. One method of obtaining such positional information involves scanning the neutron beam across the surface of the object under interrogation. There are many methods for such scanning. The simplest would involve utilizing a fixed, relatively small diameter neutron beam and moving the object across the beam as for example in an X-Y coordinate matrix. Another variation of this system would involve mechanically moving the neutron source so as to scan the neutron beam across the object.

Figure 3:
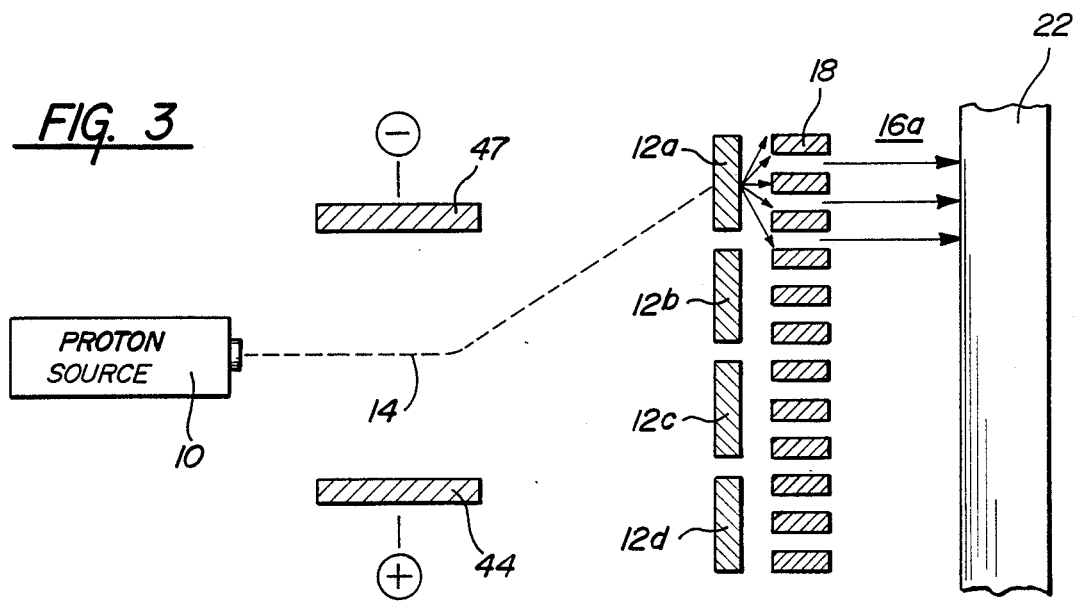
FIG. 3 is a schematic depiction of a neutron beam source as adapted to scan the surface of a closed container.

Referring now to FIG. 3 there is disclosed an alternative method for scanning a neutron beam. This method is electronic and hence allows for a very rapid beam scan. As disclosed in the figure, a proton source 10, generally similar to that previously described is employed to generate a proton beam 14, which beam is steered by a pair of electrode plates 47, 44. The scanning system further includes a plurality of targets 12a, 12b, 12c, 12d generally similar to those previously described. Each target has a collimator 18 proximate thereto. In this manner, each target is a separate neutron generating system adapted to generate a relatively small area neutron beam 16a when struck by a proton beam 14. As should be apparent, the neutron beam 16a can be swept across the surface of the object 22 being interrogated by simply steering the proton beam 14 from one target to another. For example, in the apparatus of FIG. 3, the charge on the two electrode plates 47, 44 is varied so as to sweep the proton beam 14 from plate 12a down to plate 12d and in so doing the neutron beam 16a is swept across the surface of the object 22 being scanned.

In order to provide for the capability of X-Y matrix scanning a matrix of small targets 12 can be arrayed in a plane and a second set of control electrodes generally similar to the first set 47, 44 is employed to sweep the proton beam 14 across the matrix of targets.

It should be kept in mind that as the neutron beam is being scanned the energy thereof will have to be varied if a resonance spectrum is to be obtained. This variation of energy may be carried out for each scan point individually, that is to say the beam 14 may be directed onto a first target, as for example target 12a and the full range of energies under investigation accessed at that time; and the beam may then be moved onto the adjacent target. In another embodiment, each of the targets in the array is swept with a first level of proton energy and then sequentially swept with succeeding energy levels. The choice of operational mode will depend upon processing software employed.

The system of the present invention may be readily modified to give three-dimensional information indicating, for example, the shape and/or position of suspect material within an object being investigated. In light of the disclosure herein, such modifications should be readily apparent to those of skill in the art and accordingly constitute a part of the present invention. Such three-dimensional information may be obtained, for example, by obtaining a first neutron signal with the object in a first orientation relative to the neutron beam and subsequently obtaining at least one more signal after the object and beam have been rotated relative to one another. Such rotation can be expediently accomplished by utilizing a movable support for the object under interrogation or alternatively, by moving the neutron beam and/or detector relative to the object. Once a plurality of such measurements have been made from differing perspectives, they may be combined electronically utilizing well-known image processing techniques so as to give three-dimensional information about the contents of the object.

Tomographic techniques have been well developed for use with X-ray and ultrasound imagers, and such techniques are readily adaptable for use with the technology disclosed herein. Tomographic information may be obtained in either a backscatter or forward scatter mode as is well-known to those of skill in the art. For example, a detector and neutron source may be mounted so as to rotate in an arc about the object, which is maintained at the center of the arc and through the use of appropriate processing software a series of tomographic images generated; likewise, the detector and neutron source may be in a fixed position and the object rotated. In accord with the other well-known principles, the object may be interrogated so as to produce a stereoscopic type of image by generating a pair of images taken from different points of view as for example, by shifting the object to the right or left relative to the incident neutron beam.

While the principles of the instant invention have primarily been described with reference to a stationary apparatus for interrogating objects, the present invention may be readily adapted to provide a mobile apparatus. Apparatus of this type may be utilized to scan relatively large objects so as to detect the presence of hidden or otherwise inaccessible materials therein.

Figure 5:
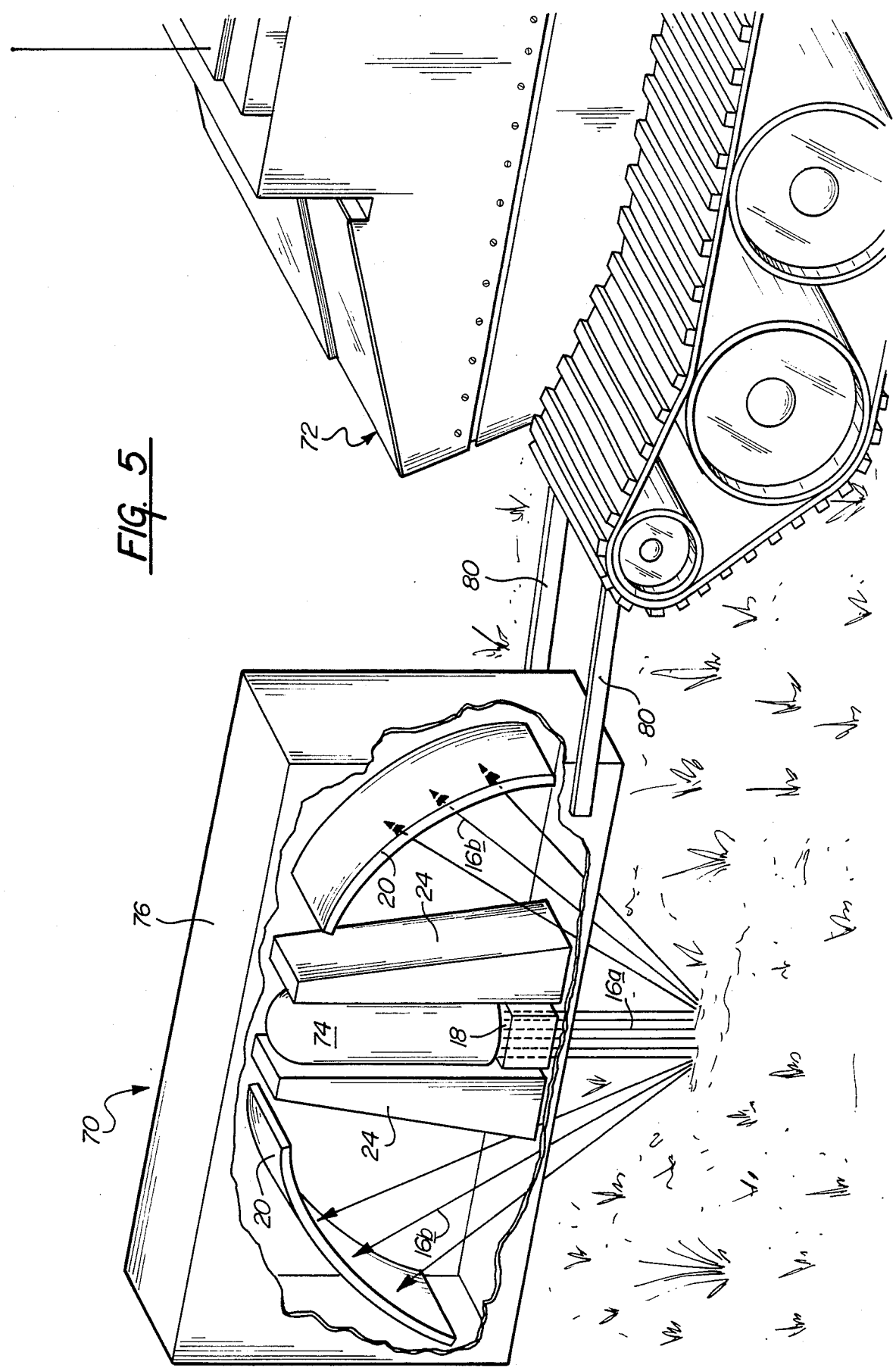
FIG. 5 is a depiction of one particular mobile form of the apparatus of the present invention as deployed to locate subterranean explosive devices.

Referring now to FIG. 5, there is shown one such embodiment of mobile scanning apparatus 70, utilized as a mine sweeping apparatus and deployed in conjunction with a tracked vehicle such as an armored personnel carrier 72.

The apparatus 70 of FIG. 5 is a portable version of the apparatus described with reference to FIG. 2 and as such, like structures will be referred to by similar reference numerals. The apparatus 70 of FIG. 5 includes a neutron source 74 having a collimator 18 associated therewith. The source and collimator cooperate to provide a relatively collimated beam of neutrons 16a directed toward the object being interrogated, in this case the surface of the earth. The apparatus further includes a pair of neutron detectors 20 generally similar to those previously described as well as neutron shielding 24 for attenuating stray signals which may reach the detector. The apparatus is housed within a container 76 shown here in cutaway view and having an opening in the bottom, not generally visible, through which the neutrons pass. It is normally preferred that the container 76 be fabricated from a neutron absorbing material so as to limit the release of stray neutrons.

It is generally preferred in a mobile apparatus of this type to remove the controller, analyzer and display from the immediate vicinity of the apparatus 70 itself and this is expediently accomplished by the use of a connecting cable or wireless data link which conveys the signals produced by the detectors 20 to remote locations for processing. As shown in this embodiment, the apparatus 70 is mounted upon a tracked vehicle 72 by means of a pair of mounting brackets 80, although obviously other such configurations may be employed.

In operation, the vehicle 72 having the apparatus 70 mounted on the front end thereof is driven across a field. The neutron source 74 projects a beam of collimated neutrons 16a onto and into the surface of the subjacent earth. Neutrons resonantly scattered from objects in the earth are captured by the detectors 20 and the signals produced thereby are processed so as to identify a resonant spectrum. Various signal processing schemes previously described may be employed in conjunction with such an embodiment, for example, ratio analysis may be utilized to precisely identify subjacent articles. However, in the instance of mine detection, it will generally be found most expedient to simply scan for large amounts of nitrogen, an element not normally found in significant amounts in the subsurface of the earth and generally indicative of explosives. A simplified apparatus may be constructed wherein the energy of the neutron beam 16a is varied in a stepwise manner over a range in which a particularly strong nitrogen resonance will occur. For example, the beam 16a may be pulsed between one of the strong nitrogen resonances, as for example 1.116 MeV and a point wherein nitrogen resonance does not occur such as for example 1.2 MeV. Indication of a relatively strong signal at a resonance point vis a vis, the non-resonance point will be taken as in indication of high nitrogen concentration. Obviously, the "off resonance" energy level must be one which will not correspond to resonance scattering by compounds normally found in soil such as water or minerals.

It may, in some instances, be desirable to employ relatively energetic neutrons, as for example 2-4 MeV or higher neutrons to enable the beam to probe deep into the subjacent earth. Such deep probing is particularly useful in searching for buried caches of explosives in underground bunkers or the like. A mine sweeping apparatus of the type described in FIG. 5 is particularly advantageous insofar as it is well adapted to find nonmetallic explosive devices. As depicted, the neutron beam 16a is shown as being relatively narrow; obviously, it is desirable to sweep the entire path of the vehicle 72, and accordingly, the apparatus 70 will be "swept" back and forth in the vehicle's path. Alternatively, the neutron source 74 will be adapted to provide a wider beam. Although the detector apparatus 70 of FIG. 5 is depicted as disposed to detect mines directly therebeneath, it may be advantageous to orient that apparatus 70 to project the neutron beam 16a forward of itself and into the earth. In this manner, the mines will be detected well in advance of the apparatus and vehicle, thereby preventing damage in the event that a mine is detonated as for example by the neutron beam or the presence of the vehicle.

Variations of the FIG. 5 apparatus may be constructed for other particular purposes. For example, the portable scanning apparatus 70 may be particularly configured to sense narcotic material and may be deployed to scan vehicles for the presence of hidden contraband therein. The apparatus may be further modified so as to be carried by a helicopter or other aircraft so as to rapidly scan buildings, water vessels and densely forested areas for mines or caches of narcotics and/or explosives. In the event that aerial scanning is utilized, use of time of flight detection techniques is considered particularly important. In a typical aerial detection mode it is anticipated that the detector will be at least 10-20 meters above the earth consequently the intervening atmosphere will present a large volume of nitrogen to the neutron beam. Use of time of flight techniques will allow for rejection of neutrons scattered by this nitrogen. These and numerous other such modifications should be readily apparent in light of the foregoing description and drawings.

Figure 4:
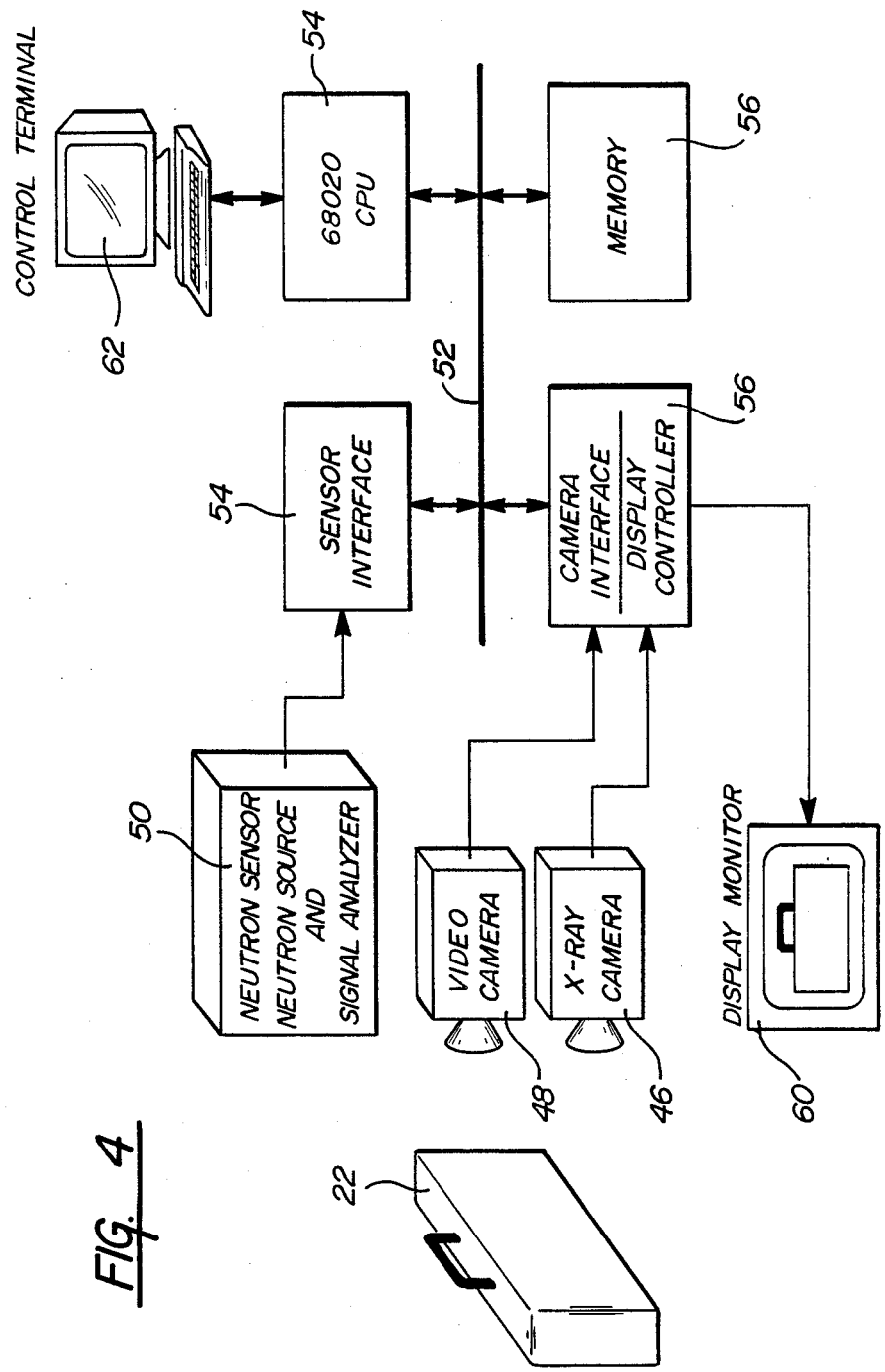
FIG. 4 is a schematic diagram of the processor architecture for a neutron backscatter inspection system of the present invention.

There are obviously many arrangements of processor architecture that may be employed in conjunction with the operation of the scanning systems of the present invention. FIG. 4 depicts the processor architecture for one such embodiment adapted for use with the FIG. 2 apparatus. As shown in the figure, the object 22 is scanned either simultaneously or sequentially by an X-ray camera 46, a video camera 48 and a neutron apparatus 50. The neutron apparatus 50 is generally similar to the system previously described and includes source, sensor and analyzer. The signal from the neutron apparatus 50 is communicated to a VME data bus 52, via a sensor interface 54 which is adapted to buffer and time the signal. The bus 52 carries the signal to a central image processor such as A 68020 CPU unit, or a CYTO computer 55 for analysis (CYTO is a registered trademark of the Environmental Research Institute of Michigan).

The signals from the video camera 48 and X-ray camera 46 are conveyed to the camera interface/display controller 56 which buffers and conditions those signals and also carries them to the data bus 52. In the central processor 55, the various signals are analyzed, compared with data from memory 57, reformatted and restored in memory. The central processor 55 configures and combines the input signal so as to produce a display signal carried to the display controller 56 via the data bus 52. The display controller 56 activates a display monitor 60 to display information generated by the system.

The display monitor may be a cathode ray or liquid crystal type display and may be configured to display overlayed visible and X-ray images together with a signal indicating location of suspect contraband. Access to the various functions of the system is preferably via a user-operated control terminal 62 having keyboard or other input device and a display device such as a cathode ray tube associated therewith.

This display capability may be employed in an inspection process analogous to X-ray inspection; however, the particular sensitivity of the technique for low atomic weight elements eliminates the difficulties encountered in applying X-ray inspection techniques for particular tasks. For example, it is desirable to nondestructively visualize explosive bodies within bombs, artillery projectiles and the like, for purposes of quality control. However, the explosive material is of low molecular weight and not readily visualized by X-rays. The present invention readily images such material allowing for accurate, noninvasive inspection.

While the foregoing description has been primarily oriented toward an imaging embodiment, it should be appreciated that the system may be simplified to give a visible or audible alarm if a material of interest is detected. Such an embodiment will be sufficient for most rapid screening systems, and may be used as a prescreen prior to utilizing a full imaging embodiment of the invention.

II. Neutron Elastic Backscatter Techniques

It has further been found in accord with the principles of the present invention that resonant scattering need not be exclusively relied upon in a neutron scatter analysis system. The energy of a neutron elastically scattered from an atom will be changed depending upon the atomic mass of the scattering atom. Accordingly, a beam of monoenergetic neutrons impinging upon an object will be scattered to provide a group of neutrons having an energy profile which is characteristic of the materials in the object. Considering the process as being analogous to the collision of billiard balls or other such rigid, generally spherically objects, it will be apparent that the magnitude of the change in energy will be greatest for those particles which are backscattered, that is to say scattered in the general direction from whence they came. It has been found that for backscattered neutrons, the following relationship holds:

$$E_{back} = E_{in}\left(\frac{A-1}{A+1}\right)^2$$

wherein $E_{Back}$ is the energy of backscattered neutrons, $E_{In}$ is the energy of the incident neutrons and A is the atomic mass of a scattering atom. As should be apparent from the formula, the change in the energy of the backscattered neutrons will depend upon the atomic mass of the scattering atom and will be greatest for lighter atoms, that is to say the neutrons scattered therefrom will have an energy which is significantly lower than the energy of the incident beam whereas neutrons backscattered from a relatively heavy atom will have an energy which is closer to that of the incident beam. This technique is a sensitive probe of atomic weight and hence may readily give data correlatable with composition.

In general, the NEBS technique of the present invention involves the impingement of a beam of neutrons (generally in the form of a pulse) onto an object and an analysis of the energy/intensity distribution (referred to generally as an energy/intensity spectrum), of the backscattered neutrons. It has been found that such spectra include a number of distinct peaks which are correlatable with the contribution to the scattering by various component elements of the target object. This NEBS technique confers some distinct advantages over the resonance techniques discussed previously insofar as interference from overlapping resonance peaks is minimized, since carbon, oxygen and nitrogen tend to have fairly distinct peaks in a backscatter spectrum. Consequently problems resultant from overlap of resonance peaks is avoided. The NEBS technique has also been found quite useful for the determination of the presence of elements having medium range molecular weights such as the alkali and transition metals as well as elements such as silicon, sulfur and phosphorous.

While the NEBS technique does not necessitate the use of neutron energies manifesting resonant scattering, it has been found advantageous in some instances to implement backscatter techniques at selected resonance energies to further elucidate information regarding the composition of a target object.

It should be noted that while the technique described herein is referred to as a backscatter technique, the general principles apply to analyses involving neutrons scattered in any direction and the invention is not meant to be limited thereto. Operation in a backscatter mode confers significant advantages insofar as the change in energy upon scattering is greatest for the backscattered neutrons and furthermore, apparatus operating in a backscatter mode is generally easy to fabricate is a mechanical sense. It has also been found that the scattering from particular atoms has both isotropic and anisotropic components depending upon the electronic configuration of the atom. For example, scattering from a nitrogen atom includes an S wave component which is relatively isotropic as well as P wave and other higher order interactions which are anisotropic. In nitrogen, as well as in various other atoms, the anisotropic component is directed in a forward and backward orientation relative to the incident beam hence, by the use of backscatter techniques a higher signal-noise ratio is obtained and sensitivity further enhanced.

Data generated from NEBS techniques may be employed in a manner generally similar to that described for the resonance techniques hereinabove. The data may be utilized to provide qualitative information regarding the presence of particular elements or molecules of interest. Such qualitative information may be obtained by searching for particular peaks, or particular combinations of peaks in a backscatter spectrum, which peaks or combinations are correlatable with species of interest. The technique may also be used in a quantitative mode to determine the amount of a particular atom in an object as well as the ratios of component atoms in an object and to thus determine the presence of explosives, narcotics or other such contraband material.

As will be explained in greater detail hereinbelow, quantitative information may be obtained by impinging incident neutron beams of different energies upon an object and comparing the resultant spectra. Such techniques are particularly useful when one of the incident beams has an energy which will produce a resonant scattering of neutrons from an element of interest. By measuring scattering spectra at such an "on resonance" energy and at an "off resonance" energy the contribution of the particular element may be readily ascertained even though various other potentially interfering species are present.

It will thus be seen that through the use of elastic backscatter techniques, significant information regarding the composition of an object may be readily obtained. Sensitivity may be further enhanced by exploiting the anisotropic nature of the scattering from various species and the energy of the incident neutron beam may be selected to establish a resonant scattering condition for particular elements of interest to still further enhance the sensitivity and selectivity of measurements made.

Figure 6:
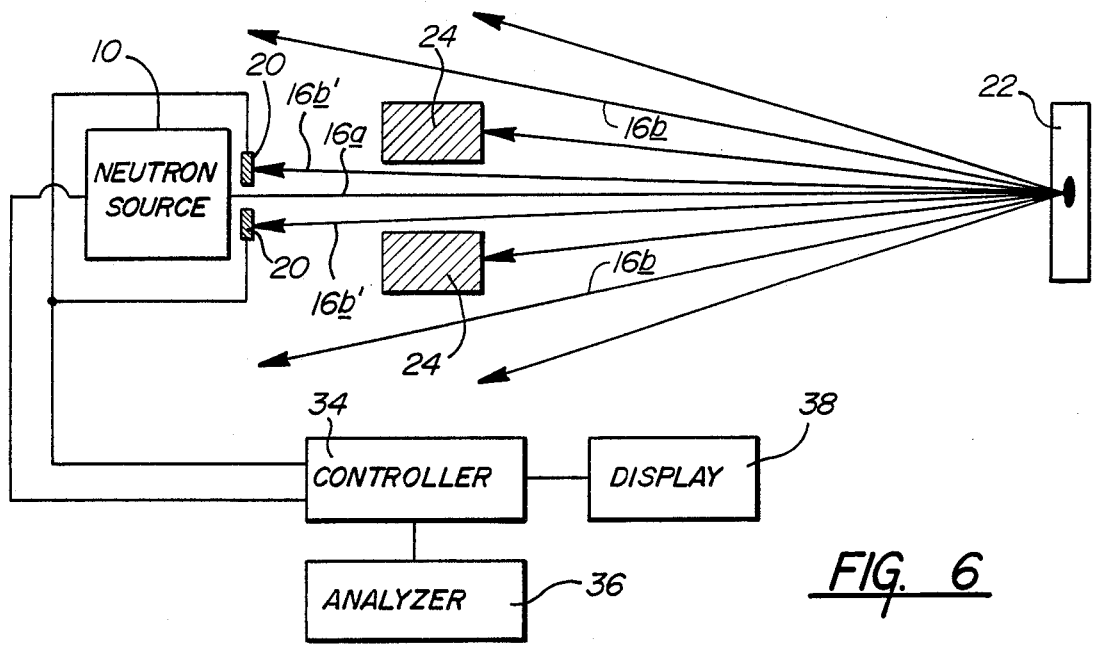
FIG. 6 is a schematic depiction of a neutron scatter apparatus structured in accord with another embodiment of the present invention as disposed to employ backscattered neutrons to interrogate an object.

Referring now to FIG. 6, there is shown a schematic view of one apparatus which may be employed to implement the neutron elastic backscatter technique herein described. The apparatus of FIG. 6 shares common elements with apparatus previously described, particularly the apparatus of FIG. 2 and hence, like elements will be referred to by the same reference numerals. The apparatus includes a neutron source 10 generally similar to that previously described and adapted to deliver a monoenergetic beam of neutrons 16a to an object 22 under inspection. The apparatus further includes one or more detectors 20, generally similar to those previously described. It will be noted however, that the detectors 20 are disposed proximate the incident beam 16a so as to receive primarily those neutrons backscattered from the object 22. In order to block all but backscattered neutrons, the detectors 20 have associated therewith neutron shields 24.

The apparatus also includes a controller 34 in operative communication with the neutron source 10 and the detectors 20. Also associated with the controller 34 is an analyzer 36 and a display 38, which are generally similar to those previously described.

In operation, the controller 34 activates the neutron source 10 to generate a monoenergetic beam of neutrons 16a, which beam is directed to the object 22 under interrogation. In order to direct and form the beam, the neutron source 10 includes therewith collimators and other such elements which have been previously described and which will not be recapitulated herein. The incident beam 16a strikes the object 22 and is scattered therefrom to produce a return beam 16b which is scattered in all directions.

The neutron shield 24 blocks the detectors 20 so that only those neutrons which are primarily backscattered, 16b' are received thereby. The detectors 20 produce a signal corresponding to the multienergetic, scattered neutrons 16b and this signal is communicated to the controller 34 and thence to the analyzer 36.

The analyzer upon receipt of the detector output signal, analyzes that signal to determine the intensity of the scattered neutrons as a function of their respective energies. By measuring the intensity of the scattered neutrons at a preselected energy, corresponding to, and indicative of, scattering of the monoenergetic beam by a preselected element, the analyzer determines the presence of that element which can be indicated by the display 38 or by some other type of audible or visual alarm.

It is generally preferred that the neutron source 10 be operated in a pulsed mode, that is to say operated so as to generate a relatively short burst of monoenergetic neutrons. It is further desired that the detectors 20 be synchronized with the proton source so as to receive only scattered neutrons from this pulse. The speed of the scattered neutrons will be determined by their energy and hence a simple time of flight technique will allow for energy resolution. Obviously, the more brief the pulse, the better will be the accuracy of the measurement of the energy of the scattered neutron, as determined by their time of flight. As the duration of the pulse decreases, the intensity of the scattered neutrons will decrease. Thus it will be appreciated that limits upon pulse duration will be imposed by pulse generation hardware and detector sensitivity. In general, pulse durations in the millisecond to nanosecond range have been found adequate in the practice of the invention. In operation, the controller activates the neutron source 10 to generate a short burst of neutrons, and the analyzer 36 operating through the controller 34 measures the intensity of the signal generated by the detector as a function of time, hence producing an energy/intensity spectrum for the backscattered neutrons. It should further be noted that by utilizing such a time of flight technique, spurious signals resultant from stray neutrons striking the detectors 20 are minimized. Such stray neutrons can result from leakage at the neutron source 10, scattering by the ambient atmosphere or by neutrons emanating from sources external of the present system.

The controller 34 may, in some embodiments, activate the neutron source 10 to sequentially generate two different pulses of neutrons, each having a different energy. The detectors 20 will then provide two separate signals each corresponding to backscattered neutrons 16b' resultant from each of the different pulses. The analyzer 36 operating through the controller 34 will, in this embodiment, analyze each of the separate signals to determine the energy/intensity spectra thereof and to analyze these spectra to obtain further information relative to the composition of the target object 22.

The principles of the NEBS technique may be further explained with reference to FIGS. 7-14 which represent actual experimental data developed utilizing the technique herein disclosed. In the experimental series, various samples of target materials of differing composition were irradiated with monoenergetic neutron beams. Backscattered neutrons were collected and analyzed utilizing a time of flight technique wherein the intensity of the backscattered neutrons was determined as a function of the time of flight of those neutrons between the sample and the detector, a time which is inversely proportional to the square root of the energy of the scattered neutrons.

Figure 7:
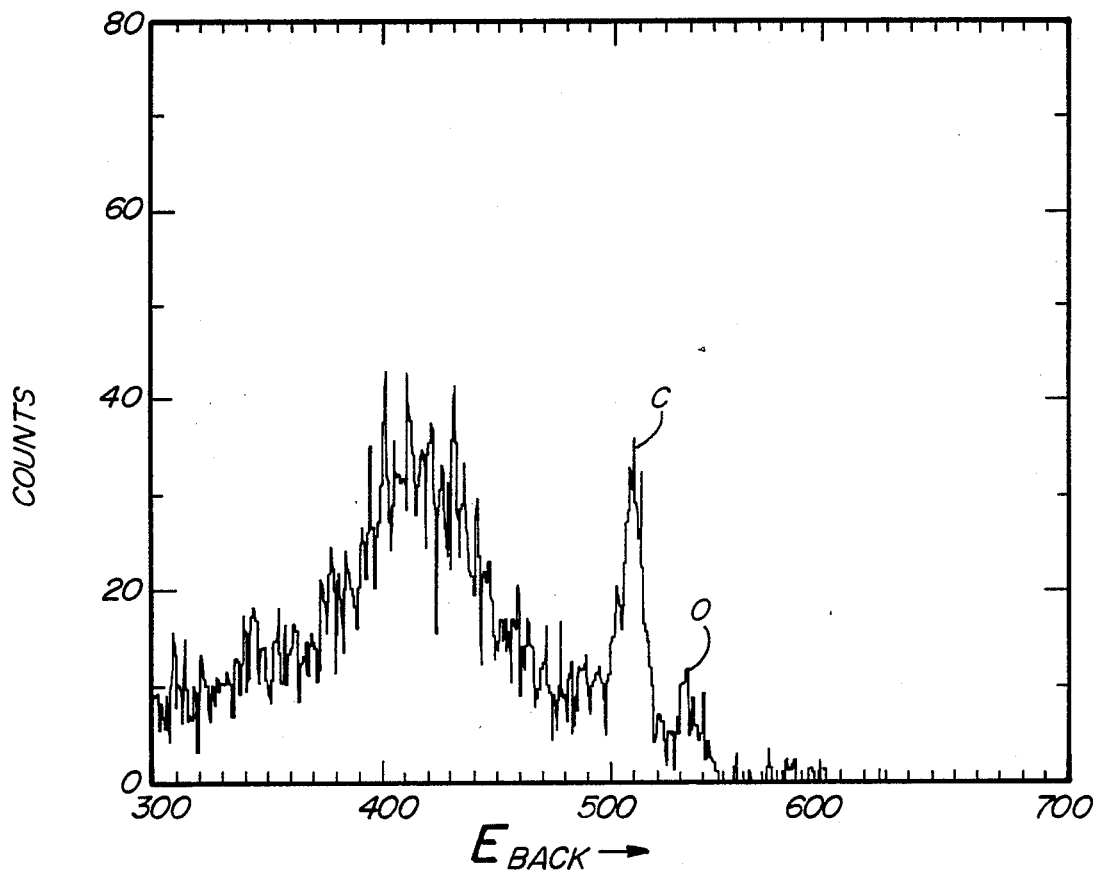
FIGS. 7–14 are representations of experimentally determined energy/intensity spectra for variously denominated, monoenergetic neutrons scattered from a number of different materials.

Referring now to FIG. 7, there is shown experimental data developed for the analysis of a sample of methyl methacrylate, a synthetic polymer consisting of carbon, hydrogen and oxygen. While this material is neither an explosive or narcotic, the principles illustrated by its analysis are obviously applicable to the detection of such materials. In the figure, there is shown a graphic representation of counts (a measure of neutron intensity) versus the energy of the backscattered neutrons. The data arrived at for FIG. 7 were obtained by irradiating the methyl methacrylate sample with neutrons of approximately 1.9 neutron MEV, a neutron energy in which resonant elastic scattering by any of the component atoms of the methyl methacrylate sample does not occur. As will be noted from the figure, there is a clutter of peaks at the low energy end of the spectrum, indicative of neutron scattering by extraneous elements of the general purpose laboratory apparatus used for the experiments.

Prominent on the chart is a first peak attributable to neutrons scattered from carbon in the sample and a second peak of smaller size attributable to scattering by oxygen atoms. For the given incident beam energy, the respective backscatter energies of the two peaks are characteristic of elastic scattering by carbon and oxygen atoms and are diagnostic for the presence of these elements within the sample under investigation. The relative intensities of the two peaks may be readily correlated via standards derived through techniques knonw in the art, with the relative amounts of the two atoms and accordingly, the ratio of carbon to oxygen may be determined.

Figure 8:
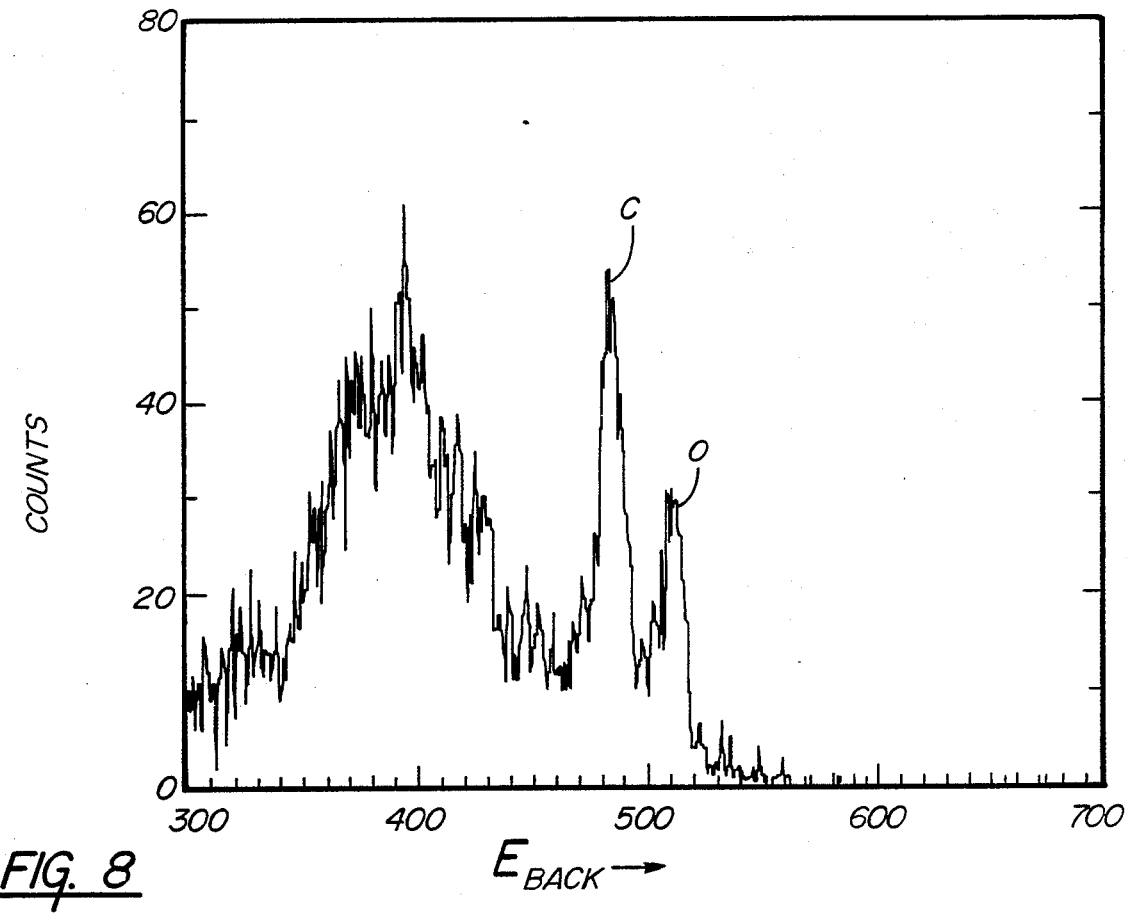

FIG. 8 is a graphic representation of data obtained from the same sample, when impinged by a neutron beam having an energy of 1.78 neutron MEV. This is a neutron energy at which resonant backscattering by nitrogen atoms occurs. Since the sample under investigation does not include nitrogen obviously, no nitrogen scattering is noticed. As in FIG. 7, the intensity/energy spectrum includes a prominent peak attributable to scattering by carbon and a second peak attributable to scattering by oxygen. It will be noted that the carbon and oxygen peak are both shifted to a lower energy position, as would be expected since the incident neutron beam is of lower energy. However, they are in a similar positional and proportional relationship to one another. And accordingly, the energy/intensity spectra of FIG. 7 and FIG. 8 are each, respectively characteristic of backscattering by methyl methacrylate. Several spectra taken at different energies may be utilized to provide a more accurate analysis of the composition of the scattering material.

Figure 9:
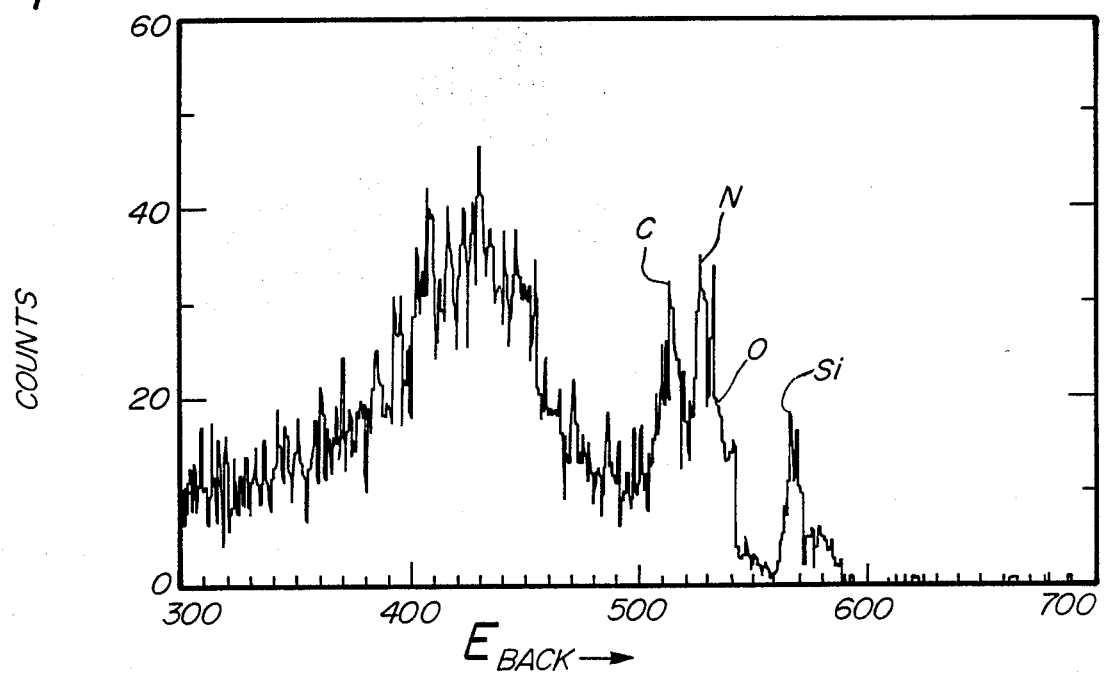

The NEBS technique may be employed for the simultaneous detection of a variety of elements in a sample. FIG. 9 is an energy/intensity spectrum for a sample of melamine reinforced with fiberglass. Melamine is a synthetic organic polymer including carbon, hydrogen and nitrogen whereas the fiberglass reinforcing material is comprised of silicon and oxygen. The sample was interrogated with a neutron beam of approximately 1.93 neutron MEV, an energy at which no resonance scattering by any of the component atoms in melamine ($C_3H_6N_6$) occurs. Data was collected as in the previous example. It will be noted from the figure that the spectrum includes prominent peaks attributable to carbon, nitrogen, oxygen and silicon. And this data may be processed as in the previous examples to obtain information regarding the relative or absolute amounts of scattering atoms present.

Figure 10:
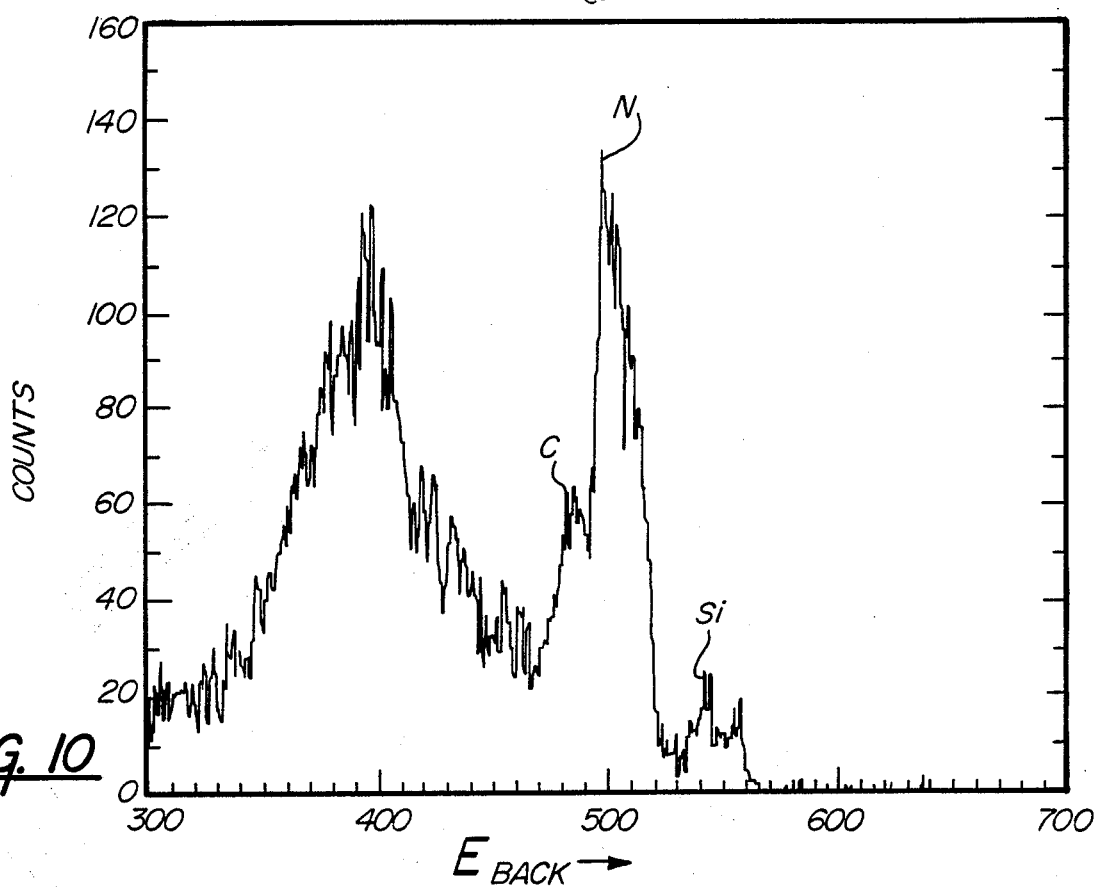

FIG. 10 is a graphic representation of the energy/intensity spectrum for the melamine-fiberglass sample, of FIG. 9, obtained with an incident beam of 1.78 neutron MEV energy. It should be noted that this energy level corresponds to the resonant scattering energy for nitrogen and accordingly, inspection of the spectrum will reveal that the peak attributable to nitrogen is significantly larger in FIG. 10 than in FIG. 9. It will also be noted that the peaks attributable to carbon, oxygen and silicon are still clearly apparent. Looking back at FIG. 9, it will be seen that the silicon peak therein is larger. There is a silicon resonance at 1.93 MEV.

Figure 11:
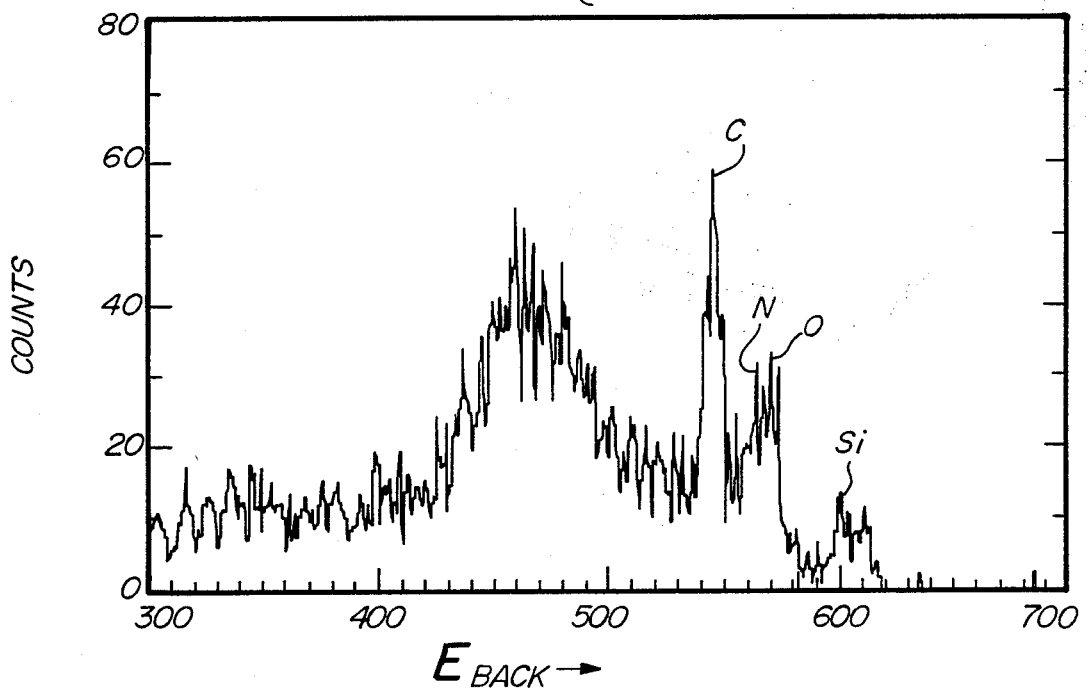

Referring now to FIG. 11, there is shown the energy/intensity spectrum for the same melamine-fiberglass sample but taken at a neutron energy of 2.078 neutron MEV, which corresponds to the resonance energy for scattering by carbon. In this instance, the magnitude of the carbon peak has grown larger than the nitrogen peak even though the carbon concentration is lower than that of nitrogen in melamine ($C_3H_6N_6$). In this figure, the carbon, nitrogen, oxygen and silicon peaks are all clearly visible.

Data such as the foregoing may be processed in a variety of ways. By comparing a spectum taken at a resonance energy of a particular element, with a spectrum obtained at a nonresonance energy and integrating the change it will be found that the integral of the change is proportional to the amount of the element whose peak is showing the change. In this manner, quantitative data may be obtained from a pair of spectra. Furthermore, by utilizing such pairs of on and off resonance data information may be obtained without the necessity for resolving the energy or time of flight of a given peak. For example, to determine the presence of nitrogen in a sample, that sample would be sequentially interrogated with neutrons having an energy corresponding to a nitrogen resonance (for example 1.78 neutron MEV) and neutrons having an energy at which resonant scattering by nitrogen does not occur, the sequence of interrogation being immaterial. If nitrogen is present a change will occur in one of the peaks in the spectrum. It will be appreciated that it need not be known which of the specific peaks corresponds to which element, or the energy of the various peaks. The presence of nitrogen in this instance is confirmed by the change in magnitude of a peak. Similar measurements may be accomplished for other elements.

Figure 12:
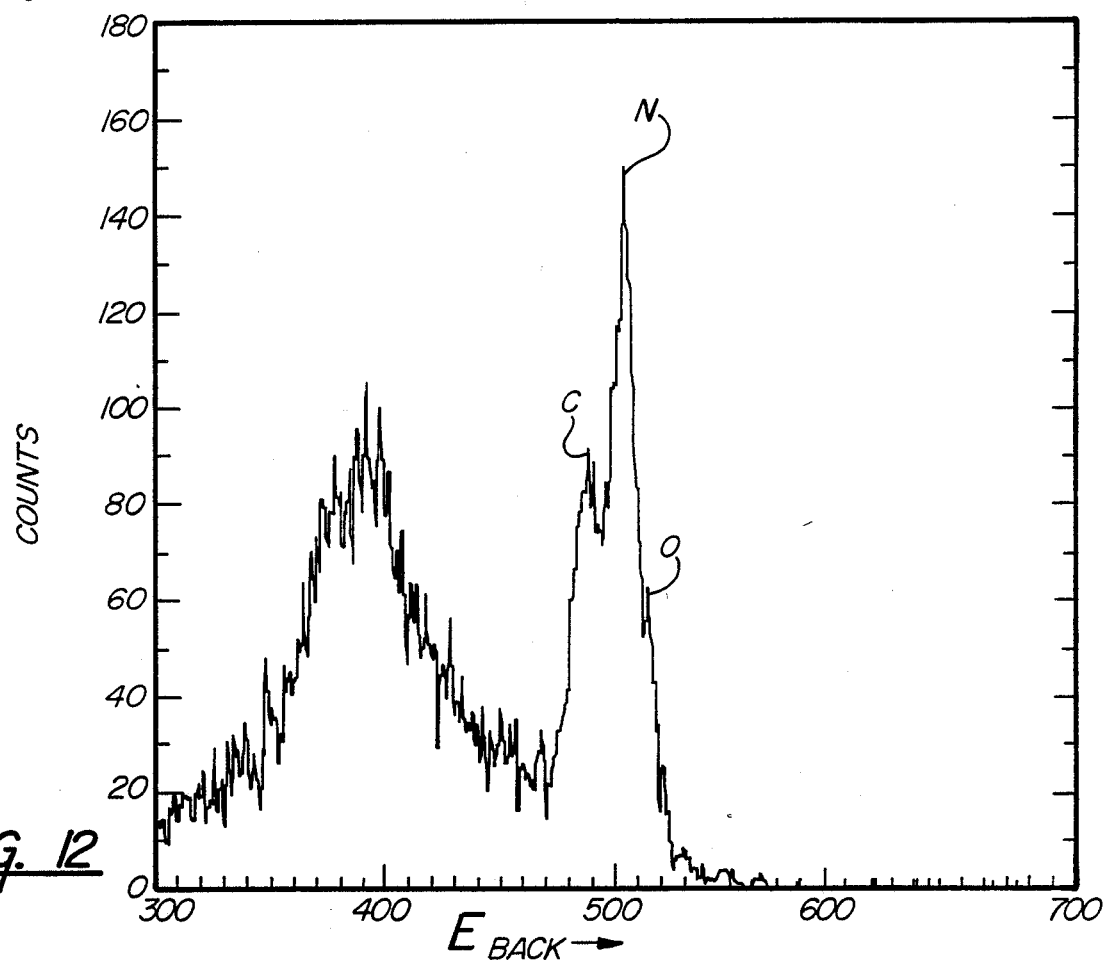

Referring now to FIG. 12, there is shown an energy/intensity spectrum for a melamine sample reinforced with cellulose (cellulose having the empirical formula $CH_2O$). This spectrum was determined at an energy of 1.78 neutron MEV and in this regard may be compared with the spectrum of FIG. 10. It is noted that the nitrogen peak is quite large owing to the resonance effect. The silicon peak is gone and the carbon peak is increased owing to the carbon added by the cellulose.

Figure 13:
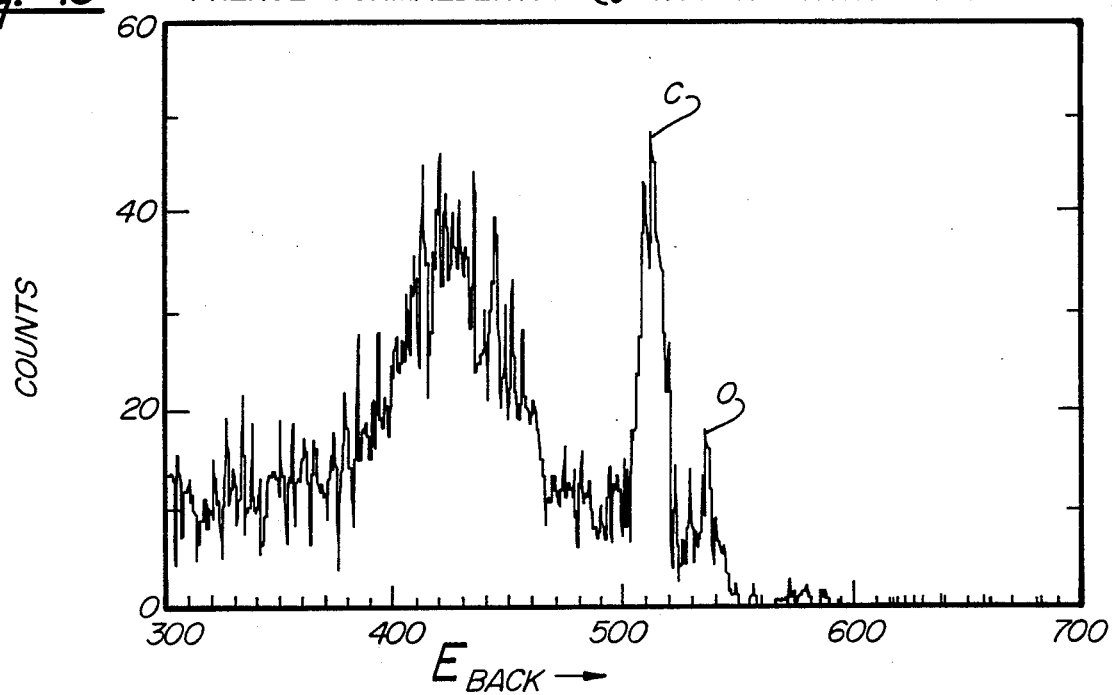
Figure 14:
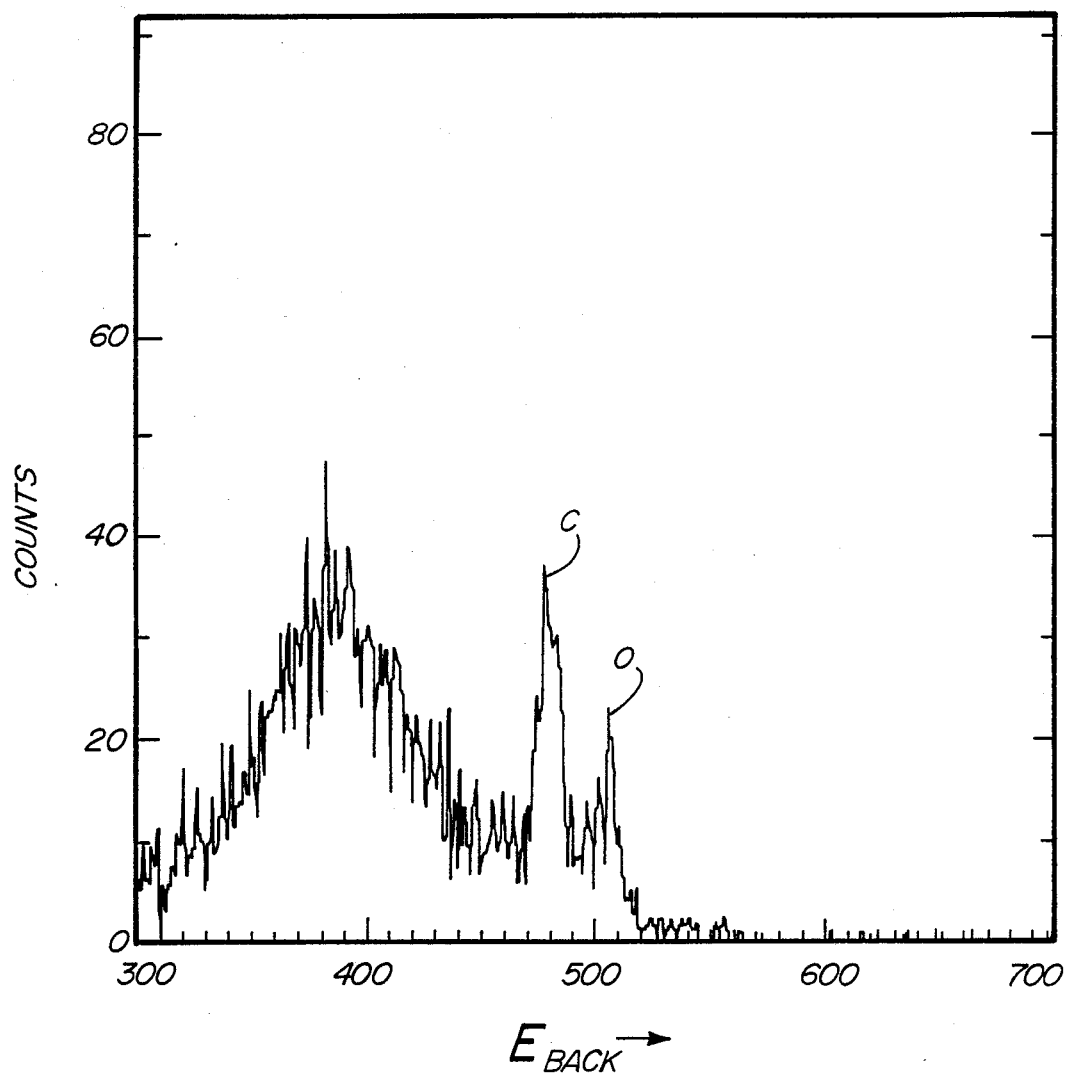

FIG. 13 and FIG. 14 depict spectra obtained for a phenol formaldehyde resin, a plastic material comprised of carbon, hydrogen and oxygen. FIG. 13 is for measurements made at a nonresonance energy, i.e. approximately 1.9 neutron MEV and FIG. 14 is for measurements made at a nitrogen resonance energy, 1.78 neutron MEV.

It should be kept in mind that while data has been presented in the foregoing examples in the form of graphic representations of energy/intensity spectra, such need not be the case for the practice of the present invention. Data may be processed by an analyzer in the form of detector output signals without the need for conversion of data into spectra. Similarly, a display associated with apparatus of the present invention may be utilized to present such data in various other human readable formats.

While apparatus is depicted as utilizing backscattered neutrons, obviously other arrangements may be employed in keeping with the present invention. Neutrons are scattered in all directions from an object and in some instances it may be more advantageous to employ other collection geometries. As was previously noted, the magnitude of the energy change upon scattering is the greatest in the reverse direction and for nitrogen and other elements of interest the anisotropic nature of the scattering frequently enhances signal intensity in the backscatter direction, making such orientation generally advantageous.

In some instances other geometries may confer similar advantages. For example, ease of equipment fabrication on installation constraints may dictate that neutrons other than those strictly backscattered be sensed by the detectors. Neutrons scattered at an angle which does not deviate by a large amount from the strictly backscattered beam will still have a significant shift in energy and such neutrons may be advantageously employed in the analysis. For example, the apparatus of FIG. 6 may have a detector mounted to receive neutrons scattered at an angle of 10 to 15 degrees from the incident beam. It may also be found in some instances that an element of interest has a strong anisotropic component of its scattering at an angle deviating from the incident beam and it may be advantageous to position a detector to sense the anisotropically scattered neutrons. The important feature of the invention is that analysis is based upon the change in energy of a monoenergetic neutron beam occasioned by collision with various atoms in a sample under interrogation.

It should also be appreciated that the apparatus described in FIGS. 3, 4 and 5 may be readily adapted for use with the NEBS mode of operation as described. Specifically, the scanning neutron source of FIG. 3 may be most advantageously employed in conjunction with a backscatter operational mode. Likewise, the package handling system of FIG. 2 and the coupled X-ray source 30 of that figure may be employed with various modes of the invention. The portable, vehicle-borne detector of FIG. 5 may be readily modified by repositioning the neutron detectors 20 to receive backscattered neutrons. Also, as mentioned the detectors may with some advantage be positioned to sense other than strictly backscattered neutrons and in such occasions the system in FIG. 5 may be modified to employ the NEBS embodiment of the present invention.

Yet other modifications are anticipated within the scope of the present invention. For example, the NEBS system as well as the NRES system may be readily adapted to an airborne mode of operation. Apparatus of this type may be carried by a helicopter on fixed-wing aircraft for purposes of scanning buildings, vehicles, land or water for contraband, explosives or other items of interest.

The foregoing drawings, description and discussion are meant to be illustrative of the principles of the present invention and not meant to be limitations upon the practice thereof. Obviously, many variations will be apparent to those skilled in the art in light of the foregoing. Accordingly, it is the following claims, including all equivalents, which define the scope of the present invention.

We claim:

1. Apparatus for the noninvasive inspection of an object to determine the presence of at least one preselected element therein, said apparatus comprising:
    a neutron beam source having a neutron beam controller operative in cooperation therewith to sequentially provide two monoenergetic neutron beams of different energies and to sequentially impinge the beams of neutrons upon the object whereby said object scatters the beams so as to provide a first and a second group of multienergetic, scattered neutrons;
    a detector disposed to receive at least a portion of each of the groups of multienergetic scattered neutrons and operative to provide a signal corresponding thereto; and
    an analyzer in communication with the detector and operative to: (1) receive the detector output signal, (2) analyze said signal to determine the intensity of the scattered neutrons as a function of their respective energies for each of the groups of scattered neutrons so as to provide an energy/intensity spectrum for each of the groups; (3) compare said spectra so as to determine the difference between the intensity of scattered neutrons of the first group at a first preselected energy indicative of the scattering of the first monoenergetic beam by a particular preselected element in said object and the intensity of scattered neutrons of the second group at a second preselected energy indicative of scattering of the second monoenergetic beam by said particular preselected element and (4) correlate said difference with the scattering contribution of said preselected element.

2. An apparatus as in claim 1, wherein said neutron beam source is adapted to generate a monoenergetic beam of neutrons having an energy corresponding to the neutron resonant scattering energy of at least one of said at least one preselected elements.

3. An apparatus as in claim 1, wherein said neutron beam source is adapted to generate a monoenergetic beam of neutrons having an energy chosen from the group consisting essentially of:
    1.78 neutron MEV, 1.908 neutron MEV, and 2.078 neutron MEV.

4. An apparatus as in claim 1, wherein said beam controller is operative to provide a first monoenergetic beam having an energy corresponding to a resonance energy of a preselected element and a second monoenergetic beam having an energy corresponding to a non-resonance value of that same preselected element.

5. An apparatus as in claim 1, wherein the scattering of the monoenergetic beams of neutrons by said at least one preselected element has an anisotropic component and wherein said detector is disposed so as to receive at least a portion of the anisotropically scattered neutrons.

6. An apparatus as in claim 1, wherein said detector is disposed so as to receive at least a portion of the neutrons backscattered by the object.

7. An apparatus as in claim 6, wherein said detector has associated therewith a shield for preventing all but backscattered neutrons from reaching it.

8. An apparatus as in claim 1, further including:
    a beam scanner adapted to scan the monoenergetic neutron beam across a plurality of scan points on the object and wherein said detector is disposed so as to receive neutrons scattered from each of said plurality of scan point.

9. A method for the non-invasive inspection of an object to determine a presence of at least one preselected element therein, the method comprising:
    providing a beam of neutrons;

controlling the energy of the neutron beam so as to sequentially provide two monoenergetic neutron beams of different energies;

sequentially impinging said beams upon the object so as to provide two groups of multienergetic scattered neutrons;

detecting at least a portion of each of said at least two groups of multienergetic scattered neutrons and providing a signal corresponding thereto;

analyzing the detector output signal so as to determine the intensity of the scattered neutrons of each said two groups as a function of their respective energies so as to provide an energy/intensity spectrum for each of the two groups;

comparing said spectra so as to determine the difference between the intensity of scattered neutrons from the first group at a first preselected energy indicative of scattering of the first monoenergetic beam by a preselected element in the object and the intensity of scattered neutrons from the second group at a second preselected energy indicative of scattering of the second monoenergetic beam by the preselected element; and correlating said difference with the scattering contribution of the preselected element.

10. A method as in claim 9, wherein the step of sequentially impinging beams of monoenergetic neutrons onto the object comprises directing a beam of neutrons having an energy corresponding to the neutron resonant scatter energy of at least one of said at least one preselected elements.

11. A method as in claim 9, wherein the step of controlling the energy of the neutron beams comprises controlling the energy so as to sequentially provide two different monoenergetic neutron beams, one of said beams having an energy corresponding to a resonant scatter energy of a preselected element and a second monoenergetic beam having an energy corresponding to a nonresonant scatter energy of that same preselected element.

12. A method as in claim 9, wherein the step of detecting at least a portion of the group of multienergetic scattered neutrons comprises detecting at least a portion of the backscattered multienergetic neutrons.

13. A method as in claim 9, wherein the step of analyzing the detector output signal includes analyzing the pulse height of the scattered neutrons as a function of their energy.

14. A method as in claim 13 wherein the step of analyzing the detector output signal further comprises analyzing the time of flight of the scattered neutrons and correlating the pulse height with the time of flight so as to spatially resolve the composition of the object.

15. Apparatus for the noninvasive inspection of an object to determine the presence of at least one preselected element therein, said apparatus comprising:

a neutron beam source for generating a monoenergetic beam of neutrons having an energy corresponding to the neutron resonant scattering energy of at least one of said at least one preselected elements and impinging that beam of neutrons upon the object whereby said object scatters the beam so as to provide a group of multienergetic, scattered neutrons;

a detector disposed to receive at least a portion of the group of multienergetic scattered neutrons and operative to provide a signal corresponding thereto; and, an analyzer in communication with the detector and operative to: (1) receive the detector output signal, (2) analyze said signal to determine the intensity of the scattered neutrons as a function of their respective energies and (3) measure the intensity of scattered neutrons at a preselected energy which is indicative of the scattering of said monoenergetic beam by one of said at least one preselected element.

16. Apparatus for the noninvasive inspection of an object to determine the presence of at least one preselected element therein, said apparatus comprising:

a neutron beam source for generating a monoenergetic beam of neutrons and impinging that beam of neutrons upon the object whereby said object scatters the beam so as to provide a group of multienergetic, scattered neutrons;

a detector disposed to receive at least a portion of the group of multienergetic scattered neutrons and operative to provide a signal corresponding thereto; and an analyzer in communication with the detector and operative to: (1) receive the detector output signal, (2) analyze said signal to determine the intensity of the scattered neutrons as a function of their respective energies and (3) measure the intensity of scattered neutrons at a preselected energy which is indicative of the scattering of said monoenergetic beam by one of said at least one preselected element.

17. An apparatus as in claim 16, wherein said object includes at least two preselected elements and wherein the analyzer is operative to measure the intensity of scattered neutrons at two preselected energies, a first energy indicative of the scattering of the monoenergetic beam by a first preselected element and the second energy indicative of scattering of the beam by a second preselected element; said analyzer further operative to correlate the intensity at said first and second preselected energies with the relative amounts of said first and second element present.

18. An apparatus as in claim 16, wherein the neutron beam source is operative to generate a monoenergetic pulse of neutrons and the analyzer is operative to measure the time of flight in which the scattered neutrons travel from the object to the detector, said time being inversely proportional to the square root of the energy of the neutrons, and to correlate said time of flight with the energy of the scattered neutrons.

19. An apparatus as in claim 16 wherein said object includes at least two preselected elements therein and wherein said analyzer is further adapted to measure the intensity of scattered neutrons at at least two preselected energies each energy indicative of the scattering of the monoenergetic beam by one of said at least two preselected elements.

20. An apparatus as in claim 19, wherein said analyzer is further adapted to determine the relative ratios of said at least two preselected elements.

21. An apparatus as in claim 16, wherein said neutron beam source includes:

a proton source adapted to provide a beam of protons having preselected energies;

a target disposed in the path of said proton beam for emitting neutrons when bombarded thereby; and a collimator disposed between the target and the object, said collimator comprising a neutron shield having an aperture therein; and a neutron beam energy controller in communication with the proton source and operative in conjunction therewith to control the energy of said protons whereby the energy of the neutrons produced by the bombardment of the target is also controlled.

22. An apparatus as in claim 21, wherein said target is fabricated from a material containing an element chosen from the group consisting essentially of: lithium, carbon, oxygen, deuterium, tritium, helium and combinations thereof.

23. An apparatus as in claim 16, wherein the neutron beam source is operative to (1) generate a short pulse of neutrons and (2) communicate with the detector so as to synchronize the operation of the detector with the generation of the short pulse of neutrons whereby the detector is adapted to only sense neutrons scattered from the short pulse.

24. Apparatus as in claim 16, wherein said analyzer is further operative to analyze the pulse height of scattered neutrons as a function of their energy.

25. Apparatus as in claim 24, wherein said analyzer is further adapted to analyze the time of flight of the scattered neutrons and correlate the pulse height with the time of flight so as to spatially resolve the composition of the object.

26. A method for the non-invasive inspection of an object to determine a presence of at least one preselected element therein, the method comprising:

directing a beam of monoenergetic neutrons having an energy corresponding to the neutron resonant scatter energy of at least one of said at least one preselected element onto the object, whereby said object scatters the beam so as to provide a group of multienergetic scattered neutrons;

detecting at least a portion of the group of multienergetic scattered neutrons and providing a signal corresponding thereto; and analyzing the detector output signal so as to determine the intensity of the scattered neutrons as a function of their respective energies and to measure the intensity of the scattered neutrons at a particular preselected energy, which energy is indicative of scattering of the monoenergetic beam by one of said at least one preselected element.

* * * * *